United States Patent
Kang et al.

(10) Patent No.: US 11,937,889 B2
(45) Date of Patent: *Mar. 26, 2024

(54) ROBOTIC SPINE SURGERY SYSTEM AND METHODS

(71) Applicant: MAKO Surgical Corp., Weston, FL (US)

(72) Inventors: Hyosig Kang, Weston, FL (US); Jienan Ding, Weston, FL (US); David Gene Bowling, Los Ranchos De Albuquerque, NM (US); Christopher Wayne Jones, Kokomo, IN (US); Greg McEwan, Mattawan, MI (US); Lucas Gsellman, Kalamazoo, MI (US)

(73) Assignee: MAKO Surgical Corp., Weston, FL (US)

(*) Notice: Subject to any disclaimer, the term of this patent is extended or adjusted under 35 U.S.C. 154(b) by 295 days.

This patent is subject to a terminal disclaimer.

(21) Appl. No.: 17/313,056

(22) Filed: May 6, 2021

(65) Prior Publication Data

US 2021/0275260 A1 Sep. 9, 2021

Related U.S. Application Data

(60) Division of application No. 16/184,376, filed on Nov. 8, 2018, now Pat. No. 11,033,341, which is a
(Continued)

(51) Int. Cl.
*A61B 34/20* (2016.01)
*A61B 17/16* (2006.01)
(Continued)

(52) U.S. Cl.
CPC .......... *A61B 34/30* (2016.02); *A61B 17/1671* (2013.01); *A61B 17/1757* (2013.01);
(Continued)

(58) Field of Classification Search
CPC ......... A61B 34/20; A61B 34/30; A61B 34/32; A61B 17/8875
See application file for complete search history.

(56) References Cited

U.S. PATENT DOCUMENTS

| | | | |
|---|---|---|---|
| 4,124,026 A | 11/1978 | Berner et al. | |
| 4,359,906 A | 11/1982 | Cordey | |

(Continued)

FOREIGN PATENT DOCUMENTS

| | | |
|---|---|---|
| CN | 201422918 Y | 3/2010 |
| CN | 201542641 U | 8/2010 |

(Continued)

OTHER PUBLICATIONS

English language abstract and machine-assisted English translation (of equivalent CN 103126767) for WO 2013/075500 extracted from espacenet.com database on Nov. 28, 2018, 12 pages.

(Continued)

*Primary Examiner* — Nicholas W Woodall
(74) *Attorney, Agent, or Firm* — Howard & Howard Attorneys PLLC

(57) ABSTRACT

A robotic system and methods for performing spine surgery are disclosed. The system comprises a robotic manipulator with a tool to hold a screw and to rotate the screw about a rotational axis. The screw is self-tapping and has a known thread geometry that is stored by one or more controllers. A navigation system tracks a position of a target anatomy. Movement of the robotic manipulator is controlled to maintain the rotational axis of the surgical tool along a planned trajectory with respect to the target anatomy based on the tracked position of the target anatomy. In autonomous or manual modes of operation, the rotational rate of the screw about the rotational axis and/or an advancement rate of the screw linearly along the planned trajectory is controlled to (Continued)

be proportional to the known thread geometry stored in the memory.

17 Claims, 12 Drawing Sheets

Related U.S. Application Data continuation-in-part of application No. 15/976,376, filed on May 10, 2018, now Pat. No. 11,065,069.

(60) Provisional application No. 62/504,019, filed on May 10, 2017.

(51) Int. Cl.
| | |
|---|---|
| *A61B 17/17* | (2006.01) |
| *A61B 17/70* | (2006.01) |
| *A61B 17/88* | (2006.01) |
| *A61B 34/00* | (2016.01) |
| *A61B 34/10* | (2016.01) |
| *A61B 34/30* | (2016.01) |
| *A61B 34/32* | (2016.01) |
| *A61B 90/98* | (2016.01) |
| *A61B 90/00* | (2016.01) |

(52) U.S. Cl.
CPC ...... *A61B 17/7076* (2013.01); *A61B 17/8875* (2013.01); *A61B 34/10* (2016.02); *A61B 34/32* (2016.02); *A61B 34/71* (2016.02); *A61B 34/76* (2016.02); *A61B 90/98* (2016.02); *A61B 17/1615* (2013.01); *A61B 17/1626* (2013.01); *A61B 17/7032* (2013.01); *A61B 17/7082* (2013.01); *A61B 17/7092* (2013.01); *A61B 2034/105* (2016.02); *A61B 2034/107* (2016.02); *A61B 34/20* (2016.02); *A61B 2034/2051* (2016.02); *A61B 2034/2055* (2016.02); *A61B 2034/2059* (2016.02); *A61B 2034/2068* (2016.02); *A61B 90/03* (2016.02); *A61B 2090/031* (2016.02); *A61B 2090/062* (2016.02); *A61B 2090/376* (2016.02)

(56) References Cited

U.S. PATENT DOCUMENTS

| | | | |
|---|---|---|---|
| 5,014,794 | A | 5/1991 | Hansson |
| 5,320,115 | A | 6/1994 | Kenna |
| 5,507,211 | A | 4/1996 | Wagner |
| 5,799,055 | A | 8/1998 | Peshkin et al. |
| 6,228,089 | B1 | 5/2001 | Wahrburg |
| 6,236,875 | B1 | 5/2001 | Bucholz et al. |
| 6,246,200 | B1 | 6/2001 | Blumenkranz et al. |
| 6,535,756 | B1 | 3/2003 | Simon et al. |
| 6,711,432 | B1 | 3/2004 | Krause et al. |
| 6,772,002 | B2 | 8/2004 | Schmidt et al. |
| 6,785,572 | B2 | 8/2004 | Yanof et al. |
| 6,823,207 | B1 | 11/2004 | Jensen et al. |
| 6,837,892 | B2 | 1/2005 | Shoham |
| 6,866,671 | B2 | 3/2005 | Tierney et al. |
| 6,877,239 | B2 | 4/2005 | Leitner et al. |
| 6,920,347 | B2 | 7/2005 | Simon et al. |
| 6,947,786 | B2 | 9/2005 | Simon et al. |
| 6,993,374 | B2 | 1/2006 | Sasso |
| 7,001,393 | B2 | 2/2006 | Schwenke et al. |
| 7,048,745 | B2 | 5/2006 | Tierney et al. |
| 7,091,683 | B1 * | 8/2006 | Smith ............ B25B 23/14 318/434 |
| 7,104,998 | B2 | 9/2006 | Yoon et al. |
| 7,107,883 | B2 | 9/2006 | Casutt |
| 7,188,626 | B2 | 3/2007 | Foley et al. |
| 7,194,120 | B2 | 3/2007 | Wicker et al. |
| 7,235,076 | B2 | 6/2007 | Pacheco |
| 7,331,965 | B2 | 2/2008 | Nielsen |
| 7,338,526 | B2 | 3/2008 | Steinberg |
| 7,396,357 | B2 | 7/2008 | Tornier et al. |
| 7,497,868 | B2 | 3/2009 | Steinberg |
| 7,542,791 | B2 | 6/2009 | Mire et al. |
| 7,570,791 | B2 | 8/2009 | Frank et al. |
| 7,587,235 | B2 | 9/2009 | Wist et al. |
| 7,607,238 | B2 | 10/2009 | Kim et al. |
| 7,630,753 | B2 | 12/2009 | Simon et al. |
| 7,637,929 | B2 | 12/2009 | Auth |
| 7,670,343 | B2 | 3/2010 | Meridew et al. |
| 7,699,877 | B2 | 4/2010 | Davison |
| 7,722,530 | B2 | 5/2010 | Davison |
| 7,725,162 | B2 | 5/2010 | Malackowski et al. |
| 7,766,930 | B2 | 8/2010 | DiPoto et al. |
| 7,799,036 | B2 | 9/2010 | Davison et al. |
| 7,822,244 | B2 | 10/2010 | Blumhofer |
| 7,831,292 | B2 | 11/2010 | Quaid et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,853,305 | B2 | 12/2010 | Simon et al. |
| 7,887,567 | B2 | 2/2011 | Shoham et al. |
| 7,900,524 | B2 | 3/2011 | Calloway et al. |
| 8,010,177 | B2 | 8/2011 | Csavoy et al. |
| 8,010,180 | B2 | 8/2011 | Quaid et al. |
| 8,010,181 | B2 | 8/2011 | Smith et al. |
| 8,016,835 | B2 | 9/2011 | Birkmeyer et al. |
| 8,036,441 | B2 | 10/2011 | Frank et al. |
| 8,046,054 | B2 | 10/2011 | Kim et al. |
| 8,052,688 | B2 | 11/2011 | Wolf, II |
| 8,057,407 | B2 | 11/2011 | Martinelli et al. |
| 8,100,950 | B2 | 1/2012 | St. Clair et al. |
| 8,133,234 | B2 | 3/2012 | Meridew et al. |
| 8,167,823 | B2 | 5/2012 | Nycz et al. |
| 8,182,469 | B2 | 5/2012 | Anderson et al. |
| 8,182,470 | B2 | 5/2012 | Devengenzo et al. |
| 8,182,491 | B2 | 5/2012 | Selover et al. |
| 8,206,405 | B2 | 6/2012 | Beverland et al. |
| 8,219,177 | B2 | 7/2012 | Smith et al. |
| 8,219,178 | B2 | 7/2012 | Smith et al. |
| 8,241,296 | B2 | 8/2012 | Wasielewski |
| 8,271,066 | B2 | 9/2012 | Sarin et al. |
| 8,277,491 | B2 | 10/2012 | Selover et al. |
| 8,311,611 | B2 | 11/2012 | Csavoy et al. |
| 8,328,852 | B2 | 12/2012 | Zehavi et al. |
| 8,335,553 | B2 | 12/2012 | Rubner et al. |
| 8,337,426 | B2 | 12/2012 | Nycz |
| 8,394,144 | B2 | 3/2013 | Zehavi et al. |
| 8,419,717 | B2 | 4/2013 | Diolaiti et al. |
| 8,425,522 | B2 | 4/2013 | Bonutti |
| 8,442,677 | B2 | 5/2013 | Shoham |
| 8,454,583 | B2 | 6/2013 | Perez-Cruet et al. |
| 8,454,619 | B1 | 6/2013 | Head |
| 8,469,963 | B2 | 6/2013 | Shoham |
| 8,491,603 | B2 | 7/2013 | Yeung et al. |
| 8,500,738 | B2 | 8/2013 | Wolf, II |
| 8,509,503 | B2 | 8/2013 | Nahum et al. |
| 8,518,051 | B2 | 8/2013 | Shoham et al. |
| 8,571,638 | B2 | 10/2013 | Shoham |
| 8,572,860 | B2 | 11/2013 | Fritzinger |
| 8,615,288 | B2 | 12/2013 | Govari et al. |
| 8,620,473 | B2 | 12/2013 | Diolaiti et al. |
| 8,634,897 | B2 | 1/2014 | Simon et al. |
| 8,657,829 | B2 | 2/2014 | McCardel |
| 8,705,829 | B2 | 4/2014 | Frank et al. |
| 8,706,185 | B2 | 4/2014 | Foley et al. |
| 8,709,016 | B2 | 4/2014 | Park et al. |
| 8,740,885 | B2 | 6/2014 | Larkin et al. |
| 8,747,476 | B2 | 6/2014 | Steinberg |
| 8,758,413 | B2 | 6/2014 | Heiges et al. |
| 8,814,877 | B2 | 8/2014 | Wasielewski |
| 8,814,914 | B2 | 8/2014 | Miller et al. |
| 8,838,205 | B2 | 9/2014 | Shoham et al. |
| 8,840,629 | B2 | 9/2014 | Bonutti |
| 8,864,752 | B2 | 10/2014 | Diolaiti et al. |
| 8,876,837 | B2 | 11/2014 | Smith et al. |
| 8,900,244 | B2 | 12/2014 | Meridew et al. |

(56) References Cited

U.S. PATENT DOCUMENTS

| | | |
|---|---|---|
| 8,911,429 B2 | 12/2014 | Olds et al. |
| 8,951,256 B2 | 2/2015 | Burroughs |
| 8,961,526 B2 | 2/2015 | Burroughs |
| 8,974,460 B2 | 3/2015 | De la Fuente Klein et al. |
| 8,979,859 B2 | 3/2015 | Leparmentier et al. |
| 8,992,580 B2 | 3/2015 | Bar et al. |
| 8,998,909 B2 | 4/2015 | Gillman et al. |
| 9,008,757 B2 | 4/2015 | Wu |
| 9,011,456 B2 | 4/2015 | Ranawat et al. |
| 9,017,313 B2 | 4/2015 | Steinberg |
| 9,042,960 B2 | 5/2015 | Neubardt |
| 9,044,190 B2 | 6/2015 | Rubner et al. |
| 9,050,108 B2 | 6/2015 | Grinberg et al. |
| 9,056,015 B2 | 6/2015 | Zehavi et al. |
| 9,066,751 B2 | 6/2015 | Sasso |
| 9,066,755 B1 | 6/2015 | Jacobs et al. |
| 9,078,685 B2 | 7/2015 | Smith et al. |
| 9,101,443 B2 | 8/2015 | Bonutti |
| 9,107,721 B2 | 8/2015 | Plotkin |
| 9,125,556 B2 | 9/2015 | Zehavi et al. |
| 9,125,680 B2 | 9/2015 | Kostrzewski et al. |
| 9,131,986 B2 | 9/2015 | Greer et al. |
| 9,138,319 B2 | 9/2015 | Fanson et al. |
| 9,149,281 B2 | 10/2015 | Bonutti |
| 9,155,544 B2 | 10/2015 | Bonutti |
| 9,161,799 B2 | 10/2015 | Benson et al. |
| 9,168,154 B2 | 10/2015 | Behzadi |
| 9,192,395 B2 | 11/2015 | Bonutti |
| 9,198,731 B2 | 12/2015 | Balaji et al. |
| 9,211,128 B2 | 12/2015 | Gillman et al. |
| 9,220,612 B2 | 12/2015 | Behzadi |
| 9,232,906 B2 | 1/2016 | Wolf, II |
| 9,237,861 B2 | 1/2016 | Nahum et al. |
| 9,240,046 B2 | 1/2016 | Carrell et al. |
| 9,241,771 B2 | 1/2016 | Kostrzewski et al. |
| 9,243,881 B2 | 1/2016 | Bourque et al. |
| 9,265,551 B2 | 2/2016 | Kust et al. |
| 9,271,741 B2 | 3/2016 | Bonutti |
| 9,271,779 B2 | 3/2016 | Bonutti |
| 9,283,048 B2 | 3/2016 | Kostrzewski et al. |
| 9,295,500 B2 | 3/2016 | Marigowda |
| 9,308,050 B2 | 4/2016 | Kostrzewski et al. |
| 9,333,042 B2 | 5/2016 | Diolaiti et al. |
| 9,339,278 B2 | 5/2016 | Meridew et al. |
| 9,339,345 B2 | 5/2016 | Song et al. |
| 9,345,387 B2 | 5/2016 | Larkin |
| 9,358,130 B2 | 6/2016 | Livorsi et al. |
| 9,398,962 B2 | 7/2016 | Steinberg |
| 9,439,675 B2 | 9/2016 | Penenberg |
| 9,452,019 B2 | 9/2016 | Schena et al. |
| 9,456,827 B2 | 10/2016 | Grinberg et al. |
| 9,462,943 B2 | 10/2016 | Brownell |
| 9,468,538 B2 | 10/2016 | Nycz et al. |
| 9,480,516 B2 | 11/2016 | Crawford et al. |
| 9,486,227 B2 | 11/2016 | Bonutti |
| 9,491,415 B2 | 11/2016 | Deitz et al. |
| 9,492,241 B2 | 11/2016 | Joskowicz et al. |
| 9,519,341 B2 | 12/2016 | Hasegawa et al. |
| 9,532,730 B2 | 1/2017 | Wasielewski |
| 9,532,849 B2 | 1/2017 | Anderson et al. |
| 9,536,309 B2 | 1/2017 | Sela et al. |
| 9,539,112 B2 | 1/2017 | Thornberry |
| 9,545,233 B2 | 1/2017 | Sirpad et al. |
| 9,545,280 B2 | 1/2017 | Crawford et al. |
| 9,549,781 B2 | 1/2017 | He et al. |
| 9,554,864 B2 | 1/2017 | Taylor et al. |
| 9,554,865 B2 | 1/2017 | Olds et al. |
| 9,561,082 B2 | 2/2017 | Yen et al. |
| 9,566,121 B2 | 2/2017 | Staunton et al. |
| 9,566,122 B2 | 2/2017 | Bowling et al. |
| 9,576,353 B2 | 2/2017 | Mahn et al. |
| 9,585,677 B2 | 3/2017 | Garcia et al. |
| 9,585,725 B2 | 3/2017 | Bonutti |
| 9,585,768 B2 | 3/2017 | Sherman et al. |
| 9,592,096 B2 | 3/2017 | Maillet et al. |
| 9,600,138 B2 | 3/2017 | Thomas et al. |
| 9,622,757 B2 | 4/2017 | Bourque et al. |
| 9,622,779 B2 | 4/2017 | Horton et al. |
| 9,629,687 B2 | 4/2017 | Bonutti |
| 9,636,162 B2 | 5/2017 | Crawford et al. |
| 9,649,160 B2 | 5/2017 | van der Walt et al. |
| 9,649,202 B2 | 5/2017 | Behzadi et al. |
| 9,655,649 B2 | 5/2017 | Shoham |
| 9,662,160 B2 | 5/2017 | Beale et al. |
| 9,662,174 B2 | 5/2017 | Taylor et al. |
| 9,668,768 B2 | 6/2017 | Piron et al. |
| 9,668,875 B2 | 6/2017 | Steinberg |
| 9,675,272 B2 | 6/2017 | Selover et al. |
| 9,687,306 B2 | 6/2017 | Markey et al. |
| 9,693,878 B2 | 7/2017 | Kunz et al. |
| 9,713,499 B2 | 7/2017 | Bar et al. |
| 9,724,167 B2 | 8/2017 | Ziaei et al. |
| 9,734,632 B2 | 8/2017 | Thomas et al. |
| 9,743,971 B2 | 8/2017 | Belkoff et al. |
| 9,743,995 B2 | 8/2017 | Lohmeier et al. |
| 9,750,510 B2 | 9/2017 | Kostrzewski et al. |
| 9,750,545 B2 | 9/2017 | Cryder et al. |
| 9,757,087 B2 | 9/2017 | Simon et al. |
| 9,782,229 B2 | 10/2017 | Crawford et al. |
| 9,788,966 B2 | 10/2017 | Steinberg |
| 9,795,319 B2 | 10/2017 | Lavallee et al. |
| 9,795,394 B2 | 10/2017 | Bonutti |
| 9,808,318 B2 | 11/2017 | Bonutti |
| 9,814,535 B2 | 11/2017 | Bar et al. |
| 9,815,206 B2 | 11/2017 | Balicki et al. |
| 9,833,292 B2 | 12/2017 | Kostrzewski et al. |
| 9,877,793 B2 | 1/2018 | Bonutti |
| 9,931,059 B2 | 4/2018 | Borja |
| 9,987,050 B2 | 6/2018 | Robinson |
| 9,987,092 B2 | 6/2018 | Hladio et al. |
| 10,004,562 B2 | 6/2018 | Kostrzewski et al. |
| RE46,954 E | 7/2018 | Pedicini |
| 10,028,722 B2 | 7/2018 | Moreau-Gaudry et al. |
| 10,028,800 B2 | 7/2018 | Bourque et al. |
| 10,034,753 B2 | 7/2018 | Dressler et al. |
| 10,076,385 B2 | 9/2018 | Shoham et al. |
| 10,080,509 B2 | 9/2018 | Wasielewski |
| 10,080,615 B2 | 9/2018 | Bartelme et al. |
| 10,085,786 B2 | 10/2018 | Chandanson et al. |
| 11,219,487 B2 | 1/2022 | He et al. |
| 2003/0173096 A1 | 9/2003 | Setton et al. |
| 2005/0149050 A1 | 7/2005 | Stifter et al. |
| 2005/0171557 A1 | 8/2005 | Shoham |
| 2006/0036264 A1 | 2/2006 | Selover et al. |
| 2006/0142657 A1 | 6/2006 | Quaid et al. |
| 2007/0058406 A1 | 3/2007 | Inoshita et al. |
| 2007/0093689 A1 | 4/2007 | Steinberg |
| 2007/0156157 A1 | 7/2007 | Nahum et al. |
| 2007/0250078 A1 | 10/2007 | Stuart |
| 2008/0004634 A1 | 1/2008 | Farritor et al. |
| 2008/0058837 A1 | 3/2008 | Steinberg |
| 2008/0071374 A1 | 3/2008 | Steinberg |
| 2008/0108994 A1 | 5/2008 | Steinberg |
| 2008/0114376 A1 | 5/2008 | Steinberg |
| 2008/0147188 A1 | 6/2008 | Steinberg |
| 2008/0281332 A1 | 11/2008 | Taylor |
| 2009/0182348 A1 | 7/2009 | Nahapetian et al. |
| 2010/0137871 A1 | 6/2010 | Borja |
| 2010/0204714 A1 | 8/2010 | Shoham |
| 2010/0241129 A1 | 9/2010 | Markey et al. |
| 2011/0015649 A1 | 1/2011 | Anvari et al. |
| 2011/0066160 A1 | 3/2011 | Simaan et al. |
| 2011/0092859 A1 | 4/2011 | Neubardt |
| 2011/0306873 A1 | 12/2011 | Shenai et al. |
| 2012/0046665 A1 | 2/2012 | Kim |
| 2012/0209117 A1 | 8/2012 | Mozes et al. |
| 2012/0283747 A1 | 11/2012 | Popovic |
| 2013/0004918 A1 | 1/2013 | Huwais |
| 2013/0307955 A1 | 11/2013 | Deitz et al. |
| 2013/0345718 A1 | 12/2013 | Crawford et al. |
| 2014/0031722 A1 | 1/2014 | Li et al. |
| 2014/0052150 A1 | 2/2014 | Taylor et al. |
| 2014/0058406 A1 | 2/2014 | Tsekos |
| 2014/0135791 A1 | 5/2014 | Nikou et al. |

(56) References Cited

U.S. PATENT DOCUMENTS

| | | |
|---|---|---|
| 2014/0135796 A1 | 5/2014 | Simon et al. |
| 2014/0180290 A1 | 6/2014 | Otto et al. |
| 2014/0222012 A1 | 8/2014 | Belkoff et al. |
| 2014/0257296 A1 | 9/2014 | Morgenstern Lopez |
| 2014/0275955 A1 | 9/2014 | Crawford et al. |
| 2014/0309560 A1 | 10/2014 | Bonutti |
| 2014/0316436 A1 | 10/2014 | Bar et al. |
| 2014/0360305 A1 | 12/2014 | Olds et al. |
| 2014/0371577 A1 | 12/2014 | Maillet et al. |
| 2014/0378999 A1 | 12/2014 | Crawford et al. |
| 2015/0031985 A1 | 1/2015 | Reddy et al. |
| 2015/0032164 A1 | 1/2015 | Crawford et al. |
| 2015/0066043 A1 | 3/2015 | Nallakrishnan |
| 2015/0100066 A1 | 4/2015 | Kostrzewski et al. |
| 2015/0112344 A1 | 4/2015 | Shoham et al. |
| 2015/0142372 A1 | 5/2015 | Singh |
| 2015/0182285 A1 | 7/2015 | Yen et al. |
| 2015/0196326 A1 | 7/2015 | Bar et al. |
| 2015/0196365 A1 | 7/2015 | Kostrzewski et al. |
| 2015/0202009 A1 | 7/2015 | Nussbaumer et al. |
| 2015/0209056 A1 | 7/2015 | Shoham et al. |
| 2015/0209119 A1 | 7/2015 | Theodore et al. |
| 2015/0223897 A1 | 8/2015 | Kostrzewski et al. |
| 2015/0223906 A1 | 8/2015 | O'Neill et al. |
| 2015/0238206 A1 | 8/2015 | Benson et al. |
| 2015/0272696 A1 | 10/2015 | Fry et al. |
| 2015/0289992 A1 | 10/2015 | Anglin et al. |
| 2015/0305817 A1 | 10/2015 | Kostrzewski |
| 2015/0313684 A1 | 11/2015 | Fanson et al. |
| 2015/0327948 A1 | 11/2015 | Schoepp et al. |
| 2015/0335386 A1 | 11/2015 | Smith et al. |
| 2015/0351860 A1 | 12/2015 | Piron et al. |
| 2015/0366624 A1* | 12/2015 | Kostrzewski .......... A61B 34/76 606/130 |
| 2016/0000512 A1 | 1/2016 | Gombert et al. |
| 2016/0008011 A1 | 1/2016 | Kostrzewski |
| 2016/0030117 A1 | 2/2016 | Mewes |
| 2016/0038238 A1 | 2/2016 | Kostrzewski et al. |
| 2016/0038242 A1 | 2/2016 | Lo Iacono et al. |
| 2016/0081753 A1 | 3/2016 | Kostrzewski |
| 2016/0081754 A1 | 3/2016 | Kostrzewski et al. |
| 2016/0081819 A1 | 3/2016 | Kelman et al. |
| 2016/0089121 A1 | 3/2016 | Stand, III et al. |
| 2016/0095631 A1 | 4/2016 | Stad |
| 2016/0095720 A1 | 4/2016 | Behzadi |
| 2016/0120612 A1 | 5/2016 | Yorimoto |
| 2016/0128789 A1 | 5/2016 | Kostrzewski et al. |
| 2016/0151120 A1 | 6/2016 | Kostrzewski et al. |
| 2016/0157941 A1 | 6/2016 | Anvari et al. |
| 2016/0175110 A1 | 6/2016 | Behzadi et al. |
| 2016/0206347 A1 | 7/2016 | Bar et al. |
| 2016/0220315 A1 | 8/2016 | Falardeau et al. |
| 2016/0220320 A1 | 8/2016 | Crawford et al. |
| 2016/0220385 A1 | 8/2016 | Falardeau et al. |
| 2016/0228133 A1 | 8/2016 | Meridew et al. |
| 2016/0235490 A1 | 8/2016 | Srivastava et al. |
| 2016/0235492 A1 | 8/2016 | Morard et al. |
| 2016/0235493 A1 | 8/2016 | LeBoeuf, II et al. |
| 2016/0242860 A1 | 8/2016 | Diolaiti et al. |
| 2016/0242934 A1 | 8/2016 | van der Walt et al. |
| 2016/0256225 A1 | 9/2016 | Crawford et al. |
| 2016/0278875 A1 | 9/2016 | Crawford et al. |
| 2016/0278941 A1 | 9/2016 | Livorsi et al. |
| 2016/0296266 A1 | 10/2016 | Chandanson et al. |
| 2016/0310218 A1 | 10/2016 | Ruckel et al. |
| 2016/0310221 A1 | 10/2016 | Bar et al. |
| 2016/0331479 A1 | 11/2016 | Crawford |
| 2016/0331481 A1 | 11/2016 | Bonutti |
| 2016/0374769 A1 | 12/2016 | Schena et al. |
| 2017/0000572 A1 | 1/2017 | Moctezuma de la Barrera et al. |
| 2017/0007334 A1 | 1/2017 | Crawford et al. |
| 2017/0020630 A1 | 1/2017 | Johnson et al. |
| 2017/0027652 A1 | 2/2017 | Johnson et al. |
| 2017/0042620 A1 | 2/2017 | Bartelme et al. |
| 2017/0055940 A1 | 3/2017 | Shoham |
| 2017/0056086 A1 | 3/2017 | Kostrzewski et al. |
| 2017/0056116 A1 | 3/2017 | Kostrzewski |
| 2017/0065428 A1 | 3/2017 | Behzadi |
| 2017/0065432 A1 | 3/2017 | Singh |
| 2017/0071682 A1 | 3/2017 | Bar et al. |
| 2017/0071685 A1 | 3/2017 | Crawford et al. |
| 2017/0071691 A1 | 3/2017 | Crawford et al. |
| 2017/0071759 A1 | 3/2017 | Behzadi et al. |
| 2017/0079727 A1 | 3/2017 | Crawford et al. |
| 2017/0086896 A1 | 3/2017 | Crawford et al. |
| 2017/0086927 A1 | 3/2017 | Auld et al. |
| 2017/0086928 A1 | 3/2017 | Auld et al. |
| 2017/0086932 A1 | 3/2017 | Auld et al. |
| 2017/0105846 A1 | 4/2017 | Behzadi |
| 2017/0119339 A1 | 5/2017 | Johnson et al. |
| 2017/0119472 A1 | 5/2017 | Herrmann et al. |
| 2017/0132789 A1 | 5/2017 | Deitz et al. |
| 2017/0143426 A1 | 5/2017 | Isaacs et al. |
| 2017/0143429 A1 | 5/2017 | Richmond et al. |
| 2017/0151025 A1 | 6/2017 | Mewes et al. |
| 2017/0156805 A1 | 6/2017 | Taylor et al. |
| 2017/0156816 A1 | 6/2017 | Ibrahim |
| 2017/0172669 A1 | 6/2017 | Berkowitz et al. |
| 2017/0172762 A1 | 6/2017 | Sherman et al. |
| 2017/0178349 A1 | 6/2017 | Ketcha et al. |
| 2017/0181774 A1 | 6/2017 | Cahill |
| 2017/0186180 A1 | 6/2017 | Piron et al. |
| 2017/0196506 A1 | 7/2017 | Behzadi |
| 2017/0196597 A1 | 7/2017 | Corbin et al. |
| 2017/0196599 A1 | 7/2017 | Kwon et al. |
| 2017/0196641 A1 | 7/2017 | Jagga et al. |
| 2017/0196701 A1 | 7/2017 | Behzadi et al. |
| 2017/0196705 A1 | 7/2017 | Behzadi |
| 2017/0196706 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0202628 A1 | 7/2017 | Dell et al. |
| 2017/0202629 A1 | 7/2017 | Maillet et al. |
| 2017/0202683 A1 | 7/2017 | Behzadi |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224358 A1 | 8/2017 | Kostrzewski |
| 2017/0231702 A1 | 8/2017 | Crawford et al. |
| 2017/0239002 A1 | 8/2017 | Crawford et al. |
| 2017/0239003 A1 | 8/2017 | Crawford et al. |
| 2017/0239006 A1 | 8/2017 | Crawford et al. |
| 2017/0239007 A1 | 8/2017 | Crawford et al. |
| 2017/0239451 A1 | 8/2017 | Berkowitz |
| 2017/0239452 A1 | 8/2017 | Berkowitz et al. |
| 2017/0245951 A1 | 8/2017 | Crawford et al. |
| 2017/0252112 A1 | 9/2017 | Crawford et al. |
| 2017/0252114 A1 | 9/2017 | Crawford et al. |
| 2017/0258469 A1 | 9/2017 | Shelton, IV et al. |
| 2017/0258533 A1 | 9/2017 | Crawford et al. |
| 2017/0258535 A1 | 9/2017 | Crawford et al. |
| 2017/0261348 A1 | 9/2017 | LeBoeuf, II et al. |
| 2017/0265774 A1 | 9/2017 | Johnson et al. |
| 2017/0281145 A1 | 10/2017 | Crawford et al. |
| 2017/0290666 A1 | 10/2017 | Behzadi |
| 2017/0296274 A1 | 10/2017 | van der Walt et al. |
| 2017/0296276 A1 | 10/2017 | Bonutti |
| 2017/0312039 A1 | 11/2017 | Crawford et al. |
| 2017/0316561 A1 | 11/2017 | Helm et al. |
| 2017/0325892 A1 | 11/2017 | Aghazadeh |
| 2017/0333057 A1 | 11/2017 | Kostrzewski et al. |
| 2017/0333136 A1 | 11/2017 | Hladio et al. |
| 2017/0333137 A1 | 11/2017 | Roessler |
| 2017/0340448 A1 | 11/2017 | Behzadi |
| 2017/0340456 A1 | 11/2017 | Behzadi |
| 2017/0348037 A1 | 12/2017 | Sexson et al. |
| 2017/0354368 A1 | 12/2017 | Behzadi |
| 2017/0354468 A1 | 12/2017 | Johnson et al. |
| 2017/0360493 A1 | 12/2017 | Zucker et al. |
| 2017/0360575 A1 | 12/2017 | Behzadi et al. |
| 2017/0367847 A1 | 12/2017 | Piriou et al. |
| 2018/0000543 A1 | 1/2018 | Hibner |
| 2018/0008324 A1 | 1/2018 | Cryder et al. |

(56) References Cited

U.S. PATENT DOCUMENTS

| | | | |
|---|---|---|---|
| 2018/0008353 A1 | 1/2018 | Kostrzewski et al. |
| 2018/0008358 A1 | 1/2018 | Kostrzewski et al. |
| 2018/0021096 A1 | 1/2018 | Kostrzewski et al. |
| 2018/0042650 A1 | 2/2018 | Gao et al. |
| 2018/0042684 A1 | 2/2018 | Kostrzewski et al. |
| 2018/0049823 A1 | 2/2018 | Shelton, IV et al. |
| 2018/0049832 A1 | 2/2018 | Eckert et al. |
| 2018/0078201 A1 | 3/2018 | Behzadi |
| 2018/0078266 A1 | 3/2018 | Fry et al. |
| 2018/0092648 A1 | 4/2018 | Sun et al. |
| 2018/0092757 A1 | 4/2018 | Behzadi et al. |
| 2018/0110573 A1 | 4/2018 | Kostrzewski |
| 2018/0147018 A1 | 5/2018 | Crawford et al. |
| 2018/0168539 A1 | 6/2018 | Singh et al. |
| 2018/0185100 A1 | 7/2018 | Weinstein et al. |
| 2018/0185107 A1 | 7/2018 | Nikou et al. |
| 2018/0193171 A1 | 7/2018 | van der Walt et al. |
| 2018/0199951 A1 | 7/2018 | Chappuis et al. |
| 2018/0199999 A1 | 7/2018 | Syverson et al. |
| 2018/0200002 A1 | 7/2018 | Kostrzewski et al. |
| 2018/0200016 A1 | 7/2018 | Chappuis et al. |
| 2018/0214223 A1 | 8/2018 | Turner |
| 2018/0221097 A1 | 8/2018 | Bonutti |
| 2018/0250077 A1 | 9/2018 | Xu et al. |
| 2018/0250144 A1 | 9/2018 | Li et al. |
| 2018/0256259 A1 | 9/2018 | Crawford |
| 2018/0263714 A1 | 9/2018 | Kostrzewski et al. |
| 2018/0325608 A1 | 11/2018 | Kang et al. |
| 2019/0090966 A1 | 3/2019 | Kang et al. |
| 2019/0269469 A1 | 9/2019 | Bush, Jr. et al. |

FOREIGN PATENT DOCUMENTS

| | | | |
|---|---|---|---|
| CN | 101700184 B | 1/2011 |
| CN | 101579269 B | 4/2011 |
| CN | 101853333 B | 11/2012 |
| CN | 105101891 A | 11/2015 |
| CN | 105169570 A | 12/2015 |
| CN | 105208962 A | 12/2015 |
| CN | 107898594 A | 4/2018 |
| JP | 2015533304 A | 11/2015 |
| NO | 2017115227 A1 | 7/2017 |
| WO | 2009092164 A1 | 7/2009 |
| WO | 2011063715 A1 | 6/2011 |
| WO | 2013075500 A1 | 5/2013 |
| WO | 2013192598 A1 | 12/2013 |
| WO | 2014077920 A1 | 5/2014 |
| WO | 2014138916 A1 | 9/2014 |
| WO | 2014139023 A1 | 9/2014 |
| WO | 2014139024 A1 | 9/2014 |
| WO | 2015061638 A1 | 4/2015 |
| WO | 2015087335 A1 | 6/2015 |
| WO | 2015115807 A1 | 8/2015 |
| WO | 2015115809 A1 | 8/2015 |
| WO | 2015166487 A1 | 11/2015 |
| WO | 2015193479 A1 | 12/2015 |
| WO | 2016008880 A1 | 1/2016 |
| WO | 2016042152 A1 | 3/2016 |
| WO | 2016088130 A1 | 6/2016 |
| WO | 2016115423 A1 | 7/2016 |
| WO | 2016118744 A1 | 7/2016 |
| WO | 2017001851 A1 | 1/2017 |
| WO | 2017023825 A1 | 2/2017 |
| WO | 2017027331 A1 | 2/2017 |
| WO | 2017035592 A1 | 3/2017 |
| WO | 2017036340 A1 | 3/2017 |
| WO | 2017037113 A1 | 3/2017 |
| WO | 2017037127 A1 | 3/2017 |
| WO | 2017048736 A1 | 3/2017 |
| WO | 2017064719 A1 | 4/2017 |
| WO | 2017121874 A2 | 7/2017 |
| WO | 2017122202 A1 | 7/2017 |
| WO | 2017123506 A1 | 7/2017 |
| WO | 2017136550 A1 | 8/2017 |
| WO | 2017123506 A9 | 9/2017 |
| WO | 2017151607 A1 | 9/2017 |
| WO | 2017162981 A1 | 9/2017 |
| WO | 2017177046 A1 | 10/2017 |
| WO | 2017218423 A1 | 12/2017 |
| WO | 2017219207 A1 | 12/2017 |
| WO | 2017219208 A1 | 12/2017 |
| WO | 2018031752 A1 | 2/2018 |
| WO | 2018072003 A1 | 4/2018 |

OTHER PUBLICATIONS

English language abstract and machine-assisted English translation for CN 101579269 extracted from espacenet.com database on Oct. 1, 2018, 11 pages.

English language abstract and machine-assisted English translation for CN 101700184 extracted from espacenet.com database on Oct. 1, 2018, 15 pages.

English language abstract and machine-assisted English translation for CN 101853333 extracted from espacenet.com database on Oct. 1, 2018, 13 pages.

English language abstract and machine-assisted English translation for CN 201422918 extracted from espacenet.com database on Oct. 1, 2018, 11 pages.

English language abstract and machine-assisted English translation for CN 201542641 extracted from espacenet.com database on Oct. 1, 2018, 15 pages.

English language abstract and machine-assisted English translation for WO 2015/115807 extracted from espacenet.com database on Nov. 28, 2018, 16 pages.

English language abstract and machine-assisted English translation for WO 2015/115809 extracted from espacenet.com database on Oct. 1, 2018, 14 pages.

English language abstract and machine-assisted English translation for WO 2017/119208 extracted from espacenet.com database on Nov. 28, 2018, 11 pages.

English language abstract and machine-assisted English translation for WO 2017/162981 extracted from espacenet.com database on Oct. 1, 2018, 13 pages.

English language abstract and machine-assisted English translation for WO 2017/219207 extracted from espacenet.com database on Nov. 28, 2018, 14 pages.

English language abstract and machine-assisted English translation of corresponding CN 101700184B for WO 2011/063715 extracted from espacenet.com database on Oct. 1, 2018, 15 pages.

English language abstract for WO 2017/036340 extracted from espacenet.com database on Oct. 3, 2018, 2 pages.

International Search Report for Application No. PCT/US2018/031999 dated Nov. 7, 2018, 5 pages.

International Search Report for Application No. PCT/US2019/060502 dated Apr. 6, 2020, 4 pages.

Invitation to Pay Additional Fees and Partial Search Report for Application No. PCT/US2018/031999 dated Sep. 12, 2018, 3 pages.

Romero, Francisco et al., "Experimental and Analytical Validation of a Modular Acetabular Prosthesis in Total Hip Arthroplasty", Journal of Orthopaedic Surgery and Research, May 16, 2007, pp. 1-9.

English language abstract for JP 2015-533304 A extracted from espacenet.com database on Aug. 16, 2023, 2 pages.

English language abstract for CN 105101891 A extracted from espacenet.com database on Dec. 30, 2023, 2 pages.

English language abstract and machine-assisted English translation for CN 105169570 A extracted from espacenet. com database on Dec. 30, 2023, 11 pages.

English language abstract for CN 105208962 A extracted from espacenet.com database on Dec. 30, 2023, 2 pages.

English language abstract and machine-assisted English translation for CN 107898594 A extracted from espacenet. com database on Dec. 30, 2023, 7 pages.

* cited by examiner

ROBOTIC SPINE SURGERY SYSTEM AND METHODS

CROSS-REFERENCE TO RELATED APPLICATIONS

This application is a divisional of U.S. Non-Provisional patent application Ser. No. 16/184,376, filed Nov. 8, 2018, which is a continuation-in-part claiming priority to and the benefit of U.S. Non-Provisional patent application Ser. No. 15/976,376, filed May 10, 2018, which claims priority to and the benefit of U.S. Provisional Patent Application No. 62/504,019, filed on May 10, 2017, the entire contents and disclosure of which are hereby incorporated herein by reference.

BACKGROUND

Robotic systems for performing surgical procedures in a patient's spine are well known. For instance, robotic systems are currently utilized to place pedicle screws in a patient's spine.

When a patient requires surgery that involves placing pedicle screws, pre-operative imaging and/or intra-operative imaging is often employed to visualize the patient's anatomy that requires treatment—in this case the patient's spine. A surgeon then plans where to place the pedicle screws with respect to the images and/or with respect to a 3-D model created from the images. Planning includes determining a position and orientation (i.e., pose) of each pedicle screw with respect to the particular vertebra in which they are being placed, e.g., by identifying the desired pose in the images and/or the 3-D model. Once the plan is set, then the plan is transferred to the robotic system for execution.

Typically, the robotic system comprises a robotic manipulator that positions a tool guide above the patient and along a desired trajectory that is aligned with the desired orientation of the pedicle screw to be placed. The robotic system also comprises a navigation system to determine a location of the tool guide with respect to the patient's anatomy so that the robotic manipulator can place the tool guide along the desired trajectory according to the surgeon's plan. In some cases, the navigation system includes tracking devices attached to the manipulator and to the patient so that the robotic system can monitor and respond to movement of the patient during the surgical procedure by moving the tool guide as needed to maintain the desired trajectory.

Once the tool guide has been positioned in alignment with the desired trajectory, the robotic manipulator is controlled to maintain the alignment. Thereafter, a surgeon positions a cannula through the tool guide and adjacent to the vertebra. The surgeon inserts a conventional drilling tool into the cannula to drill a pilot hole for the pedicle screw. The surgeon then removes the drilling tool and drives the pedicle screw into position in the pilot hole with a pedicle screw driver. In this methodology, the robotic manipulator is somewhat underutilized as the robotic manipulator plays little to no role in drilling the pilot hole or inserting the pedicle screw.

SUMMARY

In one embodiment, a surgical robotic system is provided that comprises a robotic manipulator and a surgical tool to be coupled to the robotic manipulator to rotate about a rotational axis to place an implant in a spine of a patient. A robotic controller is coupled to the robotic manipulator to control movement of the surgical tool to place the rotational axis along a desired trajectory, maintain the rotational axis along the desired trajectory, and control installation of the implant in the spine of the patient so that the implant is placed at a desired location. The robotic controller is configured to cause autonomous movement of the surgical tool to place the implant in the spine of the patient until the implant is within a predefined distance of the desired location, and thereafter, the robotic controller is configured to control manual manipulation of the surgical tool until the implant is placed at the desired location.

In another embodiment, a method is provided for placing an implant in a spine of a patient using a surgical robotic system comprising a robotic manipulator and a surgical tool coupled to the robotic manipulator to rotate about a rotational axis. The method comprises controlling movement of the surgical tool to place the rotational axis along a desired trajectory. The method also maintains the rotational axis along the desired trajectory and controls installation of the implant in the spine of the patient so that the implant is placed at a desired location. Controlling installation of the implant comprises causing autonomous movement of the surgical tool to place the implant in the spine of the patient until the implant is within a predefined distance of the desired location, and thereafter, controlling manual manipulation of the surgical tool until the implant is placed at the desired location.

In another embodiment, a surgical robotic system is provided that comprises a robotic manipulator and a skin incision tool to be coupled to the robotic manipulator to create an incision in skin of a patient. A skin tracker is to be attached to the skin of the patient to track the skin of the patient. A robotic controller is coupled to the robotic manipulator to control movement of the skin incision tool with respect to a haptic object. The haptic object is defined so that the incision is made at a desired location in the skin of the patient.

In another embodiment, a method is provided for forming an incision in skin of a patient using a surgical robotic system comprising a robotic manipulator, a skin incision tool to be coupled to the robotic manipulator, and a skin tracker attached to the skin of the patient to track the skin of the patient. The method comprises identifying a desired location of the incision with a pointer, while the skin tracker is attached to the patient. The method also comprises tracking movement of the desired location with a navigation system and controlling movement of the skin incision tool with respect to a haptic object. The haptic object is defined in a target coordinate system so that the incision is made at the desired location in the skin of the patient.

In another embodiment, a surgical robotic system is provided that comprises a robotic manipulator and a surgical tool to be coupled to the robotic manipulator to rotate about a rotational axis to form a hole in a spine of a patient to receive an implant. A robotic controller is coupled to the robotic manipulator to control movement of the surgical tool to place the rotational axis along a desired trajectory, maintain the rotational axis along the desired trajectory, and control formation of the hole in the spine of the patient so that the implant is placed at a desired location. The surgical tool comprises a drill to create a pilot hole for the implant and a reamer integrated into the drill and shaped to create a seat for a head of the implant.

In another embodiment, a surgical tool is provided for creating a hole to receive an implant. The surgical tool comprises a drill to create a pilot hole for the implant. The drill has a shaft with a proximal end and a distal end. A reamer is integrated into the drill at a location on the shaft spaced proximally from the distal end. The reamer is shaped to create a seat for a head of the implant.

In another embodiment, a method is provided for forming a hole in a spine of a patient with a robotic manipulator and a surgical tool coupled to the robotic manipulator to rotate about a rotational axis. The method comprises controlling movement of the surgical tool to place the rotational axis along a desired trajectory, maintain the rotational axis along the desired trajectory, and control formation of a hole in the spine of the patient so that the implant is placed at a desired location. The hole formed in the spine of the patient comprises a pilot hole for the implant and a seat for a head of the implant. At least part of the pilot hole and the seat are formed simultaneously.

In another embodiment, a surgical robotic system is provided that comprises a navigation system, a robotic manipulator, and a surgical tool to be coupled to the robotic manipulator to rotate a screw about a rotational axis, the screw being self-tapping and having a known thread geometry. The navigation system is configured to track a position of a target site. A robotic controller is coupled to the robotic manipulator and the navigation system, and comprises memory for storing the known thread geometry. The robotic controller is configured to control the movement of the robotic manipulator to maintain the rotational axis along a planned trajectory with respect to the target site based on the tracked position of the target site. The robotic controller is also configured to autonomously control the surgical tool to rotate the screw at a rotational rate about the rotational axis and to linearly advance the screw at an advancement rate along the planned trajectory wherein the rotational rate and the advancement rate are proportional to the known thread geometry stored in the memory.

In another embodiment, a method is provided for placing an screw in a target site using a surgical robotic system comprising a navigation system, a robotic manipulator, and a surgical tool coupled to the robotic manipulator to rotate the screw about a rotational axis. The method comprises holding the screw with the surgical tool, the tool being self-tapping and having a known thread geometry. The method comprises storing the known thread geometry in a memory of the robotic controller. The method comprises tracking a position of the target site with the navigation system. The method comprises controlling movement of the surgical tool to maintain the rotational axis along the planned trajectory with respect to the target site based on the tracked position of the target site. The method comprises autonomously controlling movement of the surgical tool to rotate the screw at a rotational rate about the rotational axis and to linearly advance the screw at an advancement rate along the planned trajectory wherein the rotational rate and advancement rate are proportional to the known thread geometry stored in the memory.

In another embodiment, a surgical robotic system is provided that comprises a robotic manipulator comprising a sensor. The surgical robotic system comprises a surgical tool coupled to the robotic manipulator and configured to hold a screw and to rotate the screw about a rotational axis, the screw being self-tapping and having a known thread geometry. The surgical robotic system comprises a navigation system configured to track a position of a target site. The surgical robotic system comprises a robotic controller coupled to the robotic manipulator and the navigation system and comprising a memory for storing the known thread geometry. The robotic controller is configured to control movement of the robotic manipulator to maintain the rotational axis of the surgical tool on a planned trajectory with respect to the target site based on the tracked position of the target site. The robotic controller is configured to detect, with the sensor, a force applied by a user. The robotic controller is configured to control one of a rotational rate of the screw about the rotational axis or an advancement rate of the screw linearly along the planned trajectory based on the forces applied by the user to implant the screw into the target site. The robotic controller is configured to autonomously control the other of the advancement rate or the rotational rate of the screw so that the advancement rate and the rotational rate are proportional to the force applied by the user and to the known thread geometry stored in the memory.

In another embodiment, a method is provided for placing a screw in a target site using a surgical robotic system. The surgical robotic system comprises a robotic manipulator, a navigation system, a robotic controller in communication with the robotic manipulator and the navigation system. The surgical robotic system comprises a surgical tool coupled to the robotic manipulator to rotate the screw about a rotational axis. The robotic manipulator comprises a sensor. The method comprises holding the screw with the surgical tool, the screw being self-tapping and having a known thread geometry. The method comprises storing the known thread geometry in a memory of the robotic controller. The method comprises tracking a position of the target site with the navigation system. The method comprises controlling movement of the surgical tool to maintain the rotational axis along the planned trajectory with respect to the target site based on the tracked position of the target site. The method comprises detecting, with the sensor, a force applied by a user. The method comprises controlling one of a rotational rate of the screw about the rotational axis or an advancement rate of the screw linearly along the planned trajectory based on the force applied by the user to implant the screw into the target site. The method comprises controlling, autonomously, the other of the autonomously, the other of the advancement rate or the rotational rate of the screw so that the advancement rate and the rotational rate are proportional to the force applied by the user and to the known thread geometry stored in the memory.

DETAILED DESCRIPTION

Figure 1:
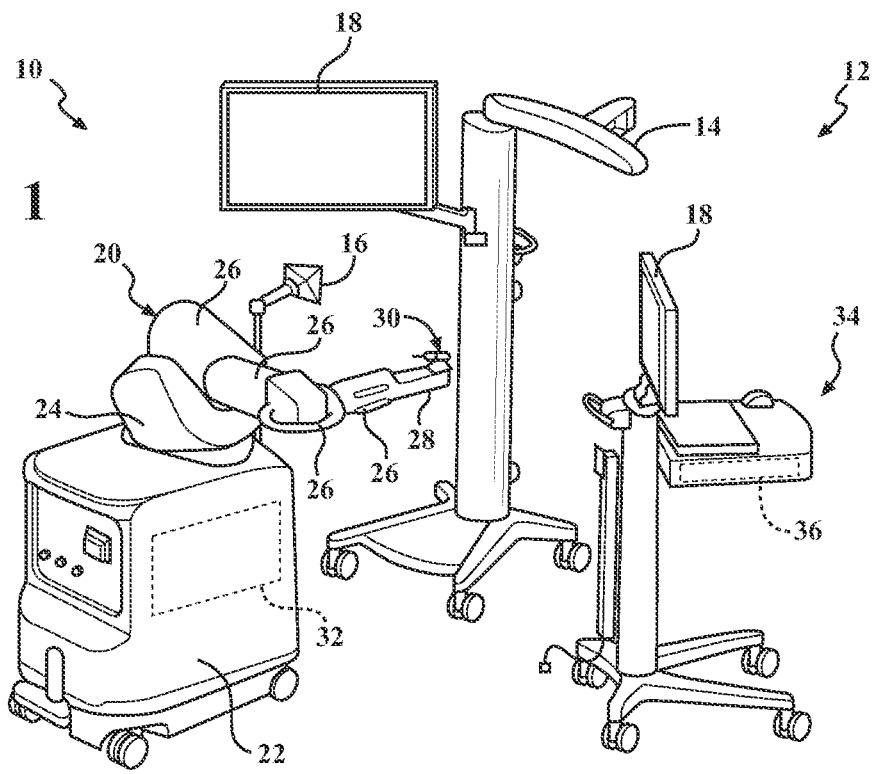
FIG. 1 is a perspective view of a robotic surgical system.
Figure 2:
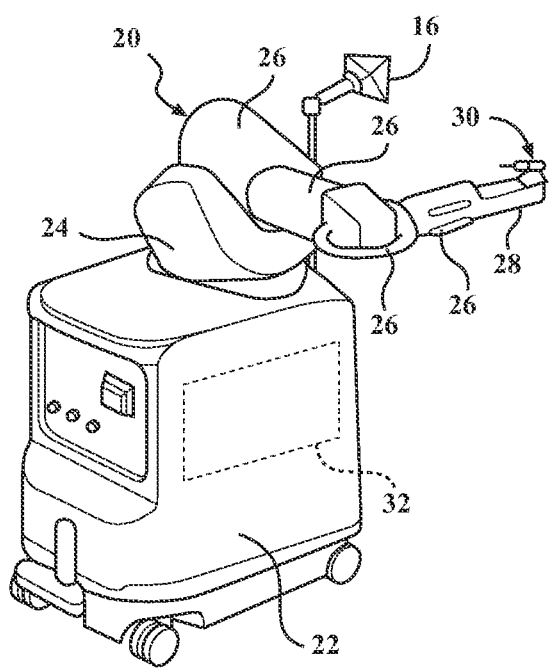
FIG. 2 is a perspective view of a surgical robotic arm used with the system of FIG. 1.

Referring to FIGS. 1 and 2, a surgical robotic system 10 is shown which can be used for various surgical procedures, including, but not limited to, spine procedures, such as spine procedures in which pedicle screws, other screws, or other types of implants are placed in the spine. The robotic system 10 comprises a navigation system 12 including a localizer 14 and a tracking device 16, one or more displays 18, and a robotic manipulator (e.g., a robotic arm 20 mounted to a base 22, a table, or the like). The robotic arm 20 includes a base link 24 rotatably coupled to the base 22 and a plurality of arm links 26 serially extending from the base link 24 to a distal end 28. The arm links 26 pivot/rotate about a plurality of joints in the robotic arm 20. A surgical tool for use in performing the spine procedure, for example, is shown generally at 30. The surgical tool 30 may be pivotally connected to the distal end 28 of the robotic arm 20.

A robotic controller 32 is configured to provide control of the robotic arm 20 or guidance to the surgeon during manipulation of the surgical tool 30. In one embodiment, the robotic controller 32 is configured to control the robotic arm 20 (e.g., by controlling joint motors thereof) to provide haptic feedback to the user via the robotic arm 20. This haptic feedback helps to constrain or inhibit the surgeon from manually moving the surgical tool 30 beyond predefined virtual boundaries associated with the surgical procedure. Such a haptic feedback system and associated haptic objects that define the virtual boundaries are described, for example, in U.S. Pat. No. 8,010,180 to Quaid et al., filed on Feb. 21, 2006, entitled "Haptic Guidance System And Method," and/or U.S. Patent Application Publication No. 2014/0180290 to Otto et al., filed on Dec. 21, 2012, entitled "Systems And Methods For Haptic Control Of A Surgical Tool," each of which is hereby incorporated by reference herein in its entirety. In one embodiment, the robotic system 10 is the RIO™ Robotic Arm Interactive Orthopedic System manufactured by MAKO Surgical Corp. of Fort Lauderdale, FL, USA.

In some embodiments, the robotic arm 20 acts autonomously based on predefined tool paths and/or other predefined movements to perform the surgical procedure. Such movements may be defined during the surgical procedure and/or before the procedure. In further embodiments, a combination of manual and autonomous control is utilized. For example, a robotic system that employs both a manual mode in which a user applies force to the surgical tool 30 to cause movement of the robotic arm 20 and a semi-autonomous mode in which the user holds a pendant to control the robotic arm 20 to autonomously follow a tool path is described in U.S. Pat. No. 9,566,122 to Bowling et al., filed on Jun. 4, 2015, and entitled "Robotic System And Method For Transitioning Between Operating Modes," hereby incorporated by reference herein in its entirety.

The navigation system 12 is set up to track movement of various objects in the operating room with respect to a target coordinate system. Such objects include, for example, the surgical tool 30, the patient's anatomy of interest, e.g., one or more vertebra, and/or other objects. The navigation system 12 tracks these objects for purposes of displaying their relative positions and orientations in the target coordinate system to the surgeon and, in some cases, for purposes of controlling or constraining movement of the surgical tool 30 relative to virtual boundaries associated with the patient's anatomy and defined with respect to the target coordinate system (e.g., via coordinate system transformations well known in surgical navigation).

The surgical navigation system 12 includes a computer cart assembly 34 that houses a navigation controller 36. The navigation controller 36 and the robotic controller 32 collectively form a control system of the robotic system 10. A navigation interface is in operative communication with the navigation controller 36. The navigation interface includes the displays 18 that are adjustably mounted to the computer cart assembly 34. Input devices such as a keyboard and mouse can be used to input information into the navigation controller 36 or otherwise select/control certain aspects of the navigation controller 36. Other input devices are contemplated including a touch screen (not shown) or voice-activation.

The localizer 14 communicates with the navigation controller 36. In the embodiment shown, the localizer 14 is an optical localizer and includes a camera unit (one example of a sensing device). The camera unit has an outer casing that houses one or more optical position sensors. In some embodiments at least two optical sensors are employed, sometimes three or more.

The optical sensors may be separate charge-coupled devices (CCD). The camera unit is mounted on an adjustable arm to position the optical sensors with a field of view of the below discussed tracking devices 16 that, ideally, is free from obstructions. In some embodiments the camera unit is adjustable in at least one degree of freedom by rotating about a rotational joint. In other embodiments, the camera unit is adjustable about two or more degrees of freedom.

The localizer 14 includes a localizer controller (not shown) in communication with the optical sensors to receive signals from the optical sensors. The localizer controller communicates with the navigation controller 36 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors communicate directly with the navigation controller 36.

Position and orientation signals and/or data are transmitted to the navigation controller 36 for purposes of tracking the objects. The computer cart assembly 34, the displays 18, and the localizer 14 may be like those described in U.S. Pat. No. 7,725,162 to Malackowski, et al. issued on May 25, 2010, entitled "Surgery System," hereby incorporated by reference.

The robotic controller 32 and the navigation controller 36 may each, or collectively, comprise one or more personal computers or laptop computers, memory suitable for storage of data and computer-readable instructions, such as local memory, external memory, cloud-based memory, random access memory (RAM), non-volatile RAM (NVRAM), flash memory, or any other suitable form of memory. The robotic controller 32 and the navigation controller 36 may each, or collectively, comprise one or more processors, such as microprocessors, for processing instructions or for processing algorithms stored in memory to carry out the functions described herein. The processors can be any type of processor, microprocessor or multi-processor system. Additionally or alternatively, the robotic controller 32 and the navigation controller 36 may each, or collectively, comprise one or more microcontrollers, field programmable gate arrays, systems on a chip, discrete circuitry, and/or other suitable hardware, software, or firmware that is capable of carrying out the functions described herein. The robotic controller 32 and the navigation controller 36 may be carried by the robotic manipulator, the computer cart assembly 34, and/or may be mounted to any other suitable location. The robotic controller 32 and/or the navigation controller 36 is loaded with software as described below. The software converts the signals received from the localizer 14 into data representative of the position and orientation of the objects being tracked.

Figure 3:
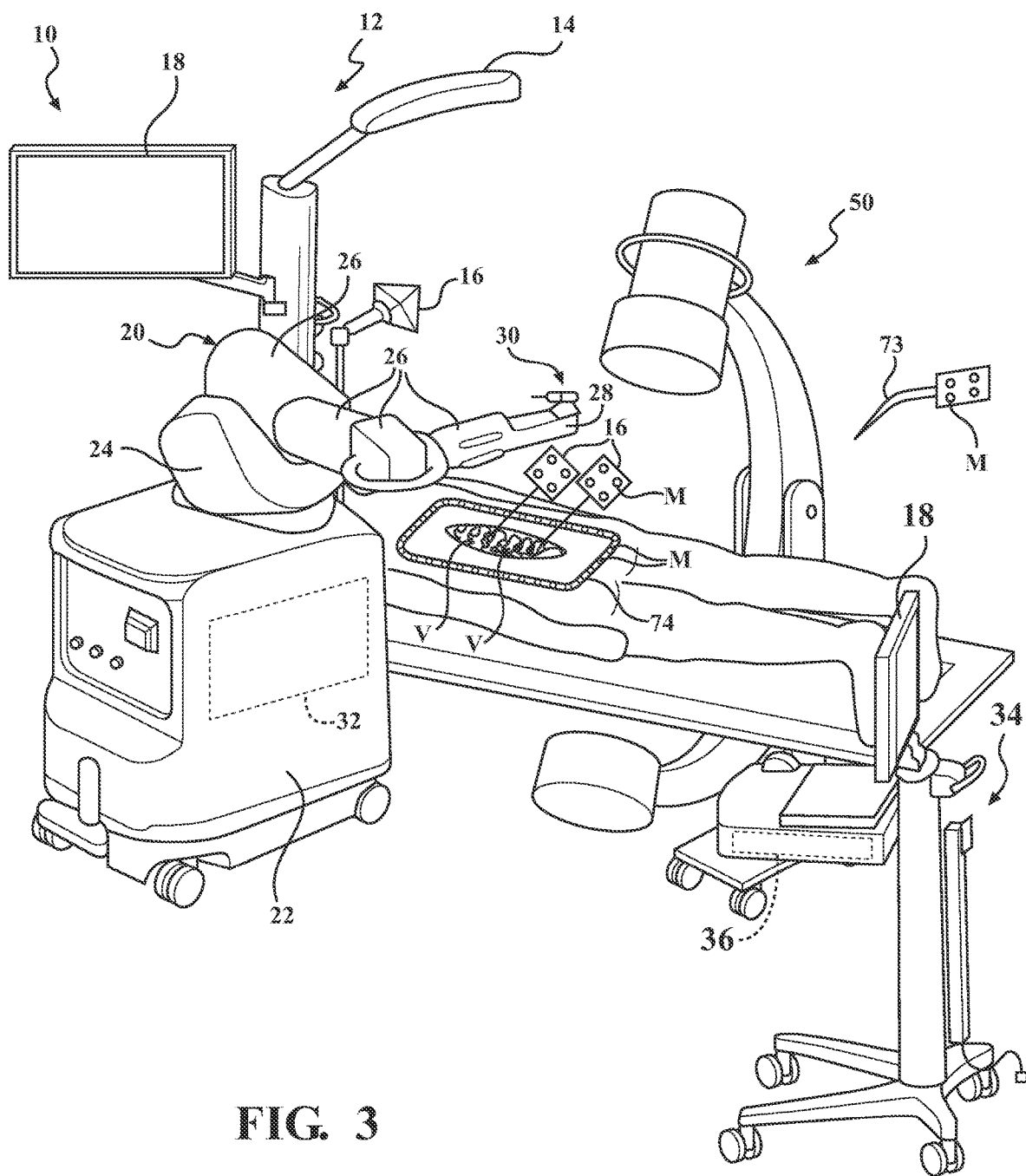
FIG. 3 is a perspective view of the robotic surgical system being used in combination with an imaging device to perform a spine procedure.

Referring to FIG. 3, navigation system 12 includes a plurality of tracking devices 16, also referred to herein as trackers. In the illustrated embodiment, trackers 16 are coupled to separate vertebra of the patient. In some cases, the trackers 16 are firmly affixed to sections of bone via bone screws, bone pins, or the like. In other cases, clamps on the spinous process or other portion of the spine may be used to attach the trackers 16. In further embodiments, the trackers 16 could be mounted to other tissue types or parts of the anatomy. The position of the trackers 16 relative to the anatomy to which they are attached can be determined by registration techniques, such as point-based registration in which a digitizing probe 73 (e.g., navigation pointer with its own markers) is used to touch off on bony landmarks on the bone or to touch on several points on the bone for surface-based registration. Conventional registration techniques can be employed to correlate the pose of the trackers 16 to the patient's anatomy, e.g., the vertebra V being treated.

Other types of registration are also possible such as using trackers 16 with mechanical clamps that attach to the spinous process of the vertebra V and that have tactile sensors (not shown) to determine a shape of the spinous process to which the clamp is attached. The shape of the spinous process can then be matched to the 3-D model of the spinous process for registration. A known relationship between the tactile sensors and the three or more markers on the tracking device 16 is pre-loaded into the navigation controller 36. Based on this known relationship, the positions of the markers relative to the patient's anatomy can be determined.

A base tracker 16 is also coupled to the base 22 to track the pose of the surgical tool 30. In other embodiments, a separate tracker 16 could be fixed to the surgical tool 30, e.g., integrated into the surgical tool 30 during manufacture or may be separately mounted to the surgical tool 30 in preparation for the surgical procedures. In any case, a working end of the surgical tool 30 is being tracked by virtue of the base tracker 16 or other tracker. The working end may be a distal end of an accessory of the surgical tool 30. Such accessories may comprise a drill, a bur, a saw, an electrical ablation device, a screw driver, a tap, a surgical knife, a Jamshidi needle, or the like.

In the illustrated embodiment, the trackers 16 are passive trackers. In this embodiment, each tracker 16 has at least three passive tracking elements or markers M for reflecting light from the localizer 14 back to the optical sensors. In other embodiments, the trackers 16 are active trackers and may have light emitting diodes or LEDs transmitting light, such as infrared light to the optical sensors. Based on the received optical signals, navigation controller 36 generates data indicating the relative positions and orientations of the trackers 16 relative to the localizer 14 using conventional triangulation techniques. In some cases, more or fewer markers may be employed. For instance, in cases in which the object being tracked is rotatable about a line, two markers can be used to determine an orientation of the line by measuring positions of the markers at various locations about the line. It should be appreciated that the localizer 14 and trackers 16, although described above as utilizing optical tracking techniques, could alternatively, or additionally, utilize other tracking modalities to track the objects, such as electromagnetic tracking, radio frequency tracking, inertial tracking, combinations thereof, and the like.

It may also be desired to track the patient's skin surface to ensure that the surgical tool 30 does not inadvertently contact or penetrate the patient's skin outside of any desired incision boundaries. For this purpose, skin attached markers M, such as active or passive markers with adhesive backing may be attached to the patient's skin to define a boundary associated with the patient's skin. An array of such markers M could be provided in a peripheral ring 74 (circular, rectangular, etc.), such that the surgical procedure continues inside the ring 74 without substantially disturbing the ring 74 (i.e., the ring is placed on the patient's skin about the incision and vertebrae of interest). One suitable skin marker array is the SpineMask® tracker manufactured by Stryker Leibinger GmbH & Co. KG, Botzinger StraBe 41, D-79111 Freiburg, Germany. See also U.S. Patent Application Publication No. 2015/0327948 to Schoepp et al., entitled "Navigation System For And Method Of Tracking The Position Of A Work Target," filed on May 13, 2015, hereby incorporated herein by reference in its entirety. Other suitable skin trackers are also contemplated. The digitizing probe could also be used to map the skin surface and/or incision as well. However, once mapped, any movement of the skin would not be detected without further digitizing, whereas the attached tracker array can detect movement of the patient's skin.

Prior to the start of the surgical procedure, additional data are loaded into the navigation controller 36. Based on the position and orientation of the trackers 16 and the previously loaded data, navigation controller 36 determines the position of the working end of the surgical tool 30 and the orientation of the surgical tool 30 relative to the tissue against which the working end is to be applied. The additional data may comprise calibration data, such as geometric data relating positions and/or orientations of the trackers 16 or markers M thereof to the working end of the surgical tool 30. This calibration data may also be determined pre-operatively or intra-operatively, such as by using a calibration probe or calibration divot on a tracker 16 of known geometry to determine a position of the working end of the surgical tool 30, e.g., relative to its own tracker or to the base tracker 16. The additional data may comprise registration data, such as transformation data associating the trackers 16 to the patient's anatomy or 3-D models thereof. In some embodiments, navigation controller 36 forwards these data to the robotic controller 32. The robotic controller 32 can then use the data to control the robotic arm 20 as described in U.S. Pat. No. 8,010,180 or 9,566,122, both of which were previously incorporated by reference herein.

The navigation controller 36 also generates image signals that indicate the relative position of the working end of the surgical tool 30 to the tissue of interest. These image signals are applied to the displays 18. Displays 18, based on these signals, generate images that allow the surgeon and staff to view the relative position of the surgical tool 30 to the surgical site. The displays 18 as discussed above, may include a touch screen or other input/output device that allows entry of commands.

In the embodiment shown, using the navigation system 12, the pose of the surgical tool 30 can be determined by tracking the location of the base 22 via the base tracker 16 and calculating the pose of the surgical tool 30 based on joint encoder data from the joints of the robotic arm 20 and a known geometric relationship between the surgical tool 30 and the robotic arm 20. Ultimately, the localizer 14 and the tracking devices 16 enable the determination of the pose of the surgical tool 30 and the patient's anatomy so the navigation system 12 knows the relative relationship between the surgical tool 30 and the patient's anatomy. One such navigation system is shown in U.S. Pat. No. 9,008,757 to Wu, filed on Sep. 24, 2013, entitled "Navigation System Including Optical And Non-Optical Sensors," hereby incorporated herein by reference.

In operation, for certain surgical tasks, the user manually manipulates (e.g., moves or causes the movement of) the robotic arm 20 to manipulate the surgical tool 30 to perform the surgical procedure on the patient, such as drilling, cutting, sawing, reaming, implant installation, and the like. As the user manipulates the surgical tool 30, the navigation system 12 tracks the location of the surgical tool 30 and/or the robotic arm 20 and provides haptic feedback (e.g., force feedback) to the user to limit the user's ability to move (or cause movement of) the surgical tool 30 beyond one or more predefined virtual boundaries that are registered (or mapped) to the patient's anatomy, which results in highly accurate and repeatable drilling, cutting, sawing, reaming, and/or implant placement.

In one embodiment, the robotic arm 20 operates in a passive manner and provides haptic feedback when the surgeon attempts to move the surgical tool 30 beyond the virtual boundary. The haptic feedback is generated by one or more actuators (e.g., joint motors) in the robotic arm 20 and transmitted to the user via a flexible transmission, such as a cable drive transmission. When the robotic arm 20 is not providing haptic feedback, the robotic arm 20 is freely moveable by the user. In other embodiments, like that shown in U.S. Pat. No. 9,566,122, previously incorporated herein by reference, the robotic arm 20 is manipulated by the user in a similar manner, but the robotic arm 20 operates in an active manner. For instance, the user applies force to the surgical tool 30, which is measured by a force/torque sensor, and the robotic arm 30 emulates the user's desired movement based on measurements from the force/torque sensor. For other surgical tasks, the robotic arm 20 operates autonomously.

Figure 4:
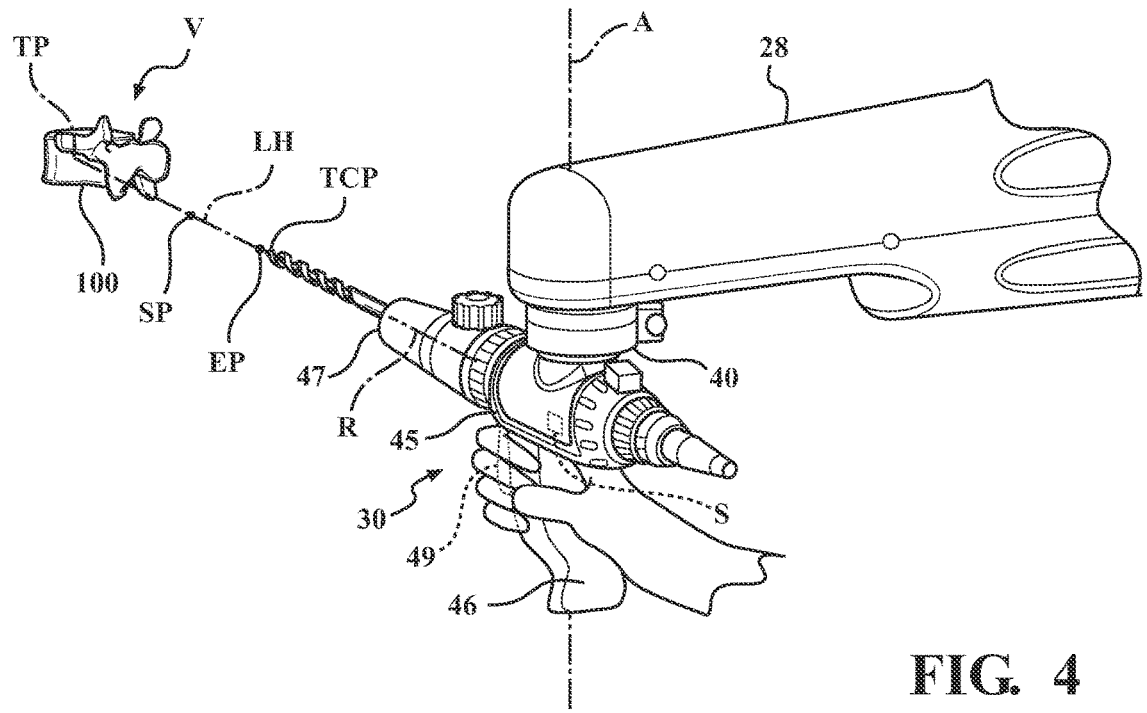
FIG. 4 is a partial perspective view of a robotic arm coupled to a surgical tool that includes a housing coupled to a drill.
Figure 5:
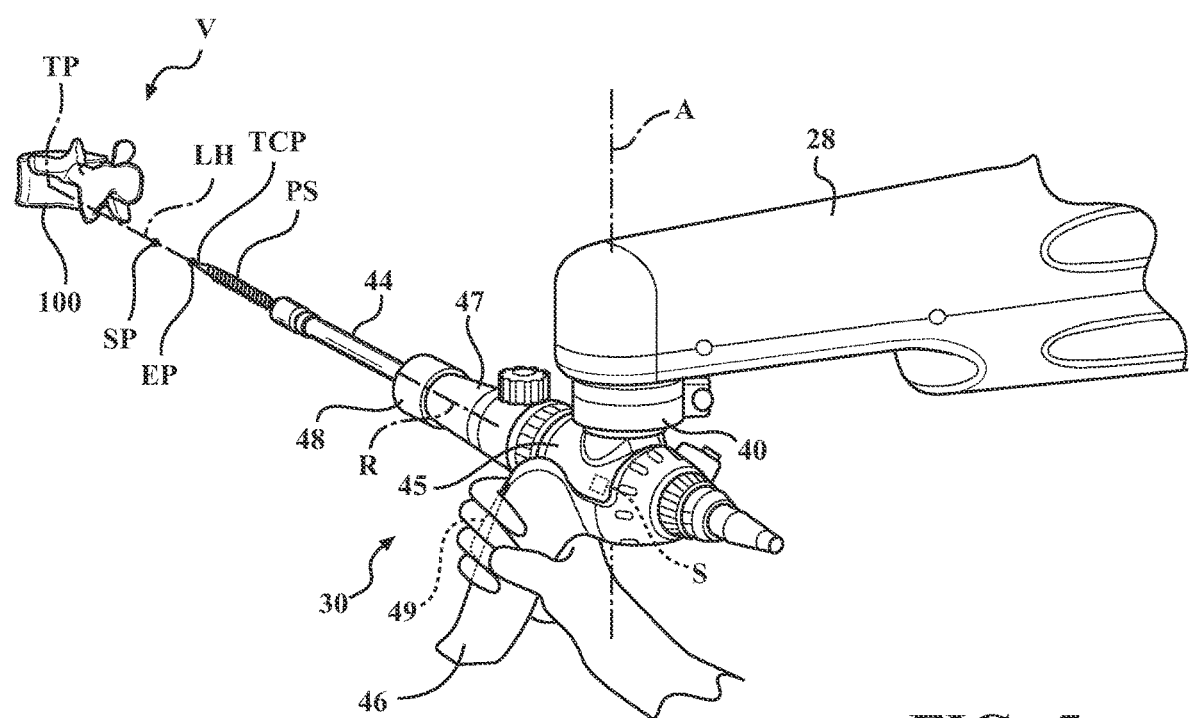
FIG. 5 is a partial perspective view of the robotic arm coupled to the surgical tool coupled to a driver and screw.

Turning to FIGS. 4 and 5, the surgical tool 30 is shown coupled to the distal end 28 of the robotic arm 20. More specifically, a coupling 40 is provided between the surgical tool 30 and the distal end 28 of the robotic arm 20 to allow rotation of the surgical tool 30 relative to the distal end 28 about axis A. In FIG. 4, the surgical tool 30 comprises a drill 42 for drilling a pilot hole for a pedicle screw, other screw, or other type of implant. The drill 42 is arranged to rotate about a rotational axis R. In FIG. 5, the surgical tool 30 comprises a driver 44 (e.g., a screw driver) arranged along the rotational axis R to rotate about the rotational axis R for driving in a pedicle screw PS or other implant.

The surgical tool 30 comprises a housing 45. A drive system (e.g., motor) is located in the housing 45 to drive the drill 42, driver 44, or other accessory. The drive system may be variable speed. A handle 46 depends from the housing 45 and includes a grip for being grasped by the user to manipulate the surgical tool 30 and/or the robotic arm 20 during the surgical procedure.

The housing 45 further comprises a collet 47 or other type of coupler for releasably attaching the drill 42, driver 44, or other accessory to the drive system. In some cases, a speed reducer 48 (see FIG. 5) may be releasably attached to the collet 47 to be used for certain accessories. The speed reducer 48 comprises a transmission or gear arrangement that causes the rotational speed of the accessory to be reduced as compared to being connected directly to the drive system. This is useful in cases where slower rotational speeds are desired. A trigger 49 may also be present to control a speed of the drill 42 and/or driver 44, to initiate movement of the robotic arm 20, to align the rotational axis R with a desired trajectory, or the like. The trigger 49 may communicate signals to the robotic controller 32 (which may include a tool controller) to control the robotic arm 20 and/or the surgical tool 30.

Figure 6:
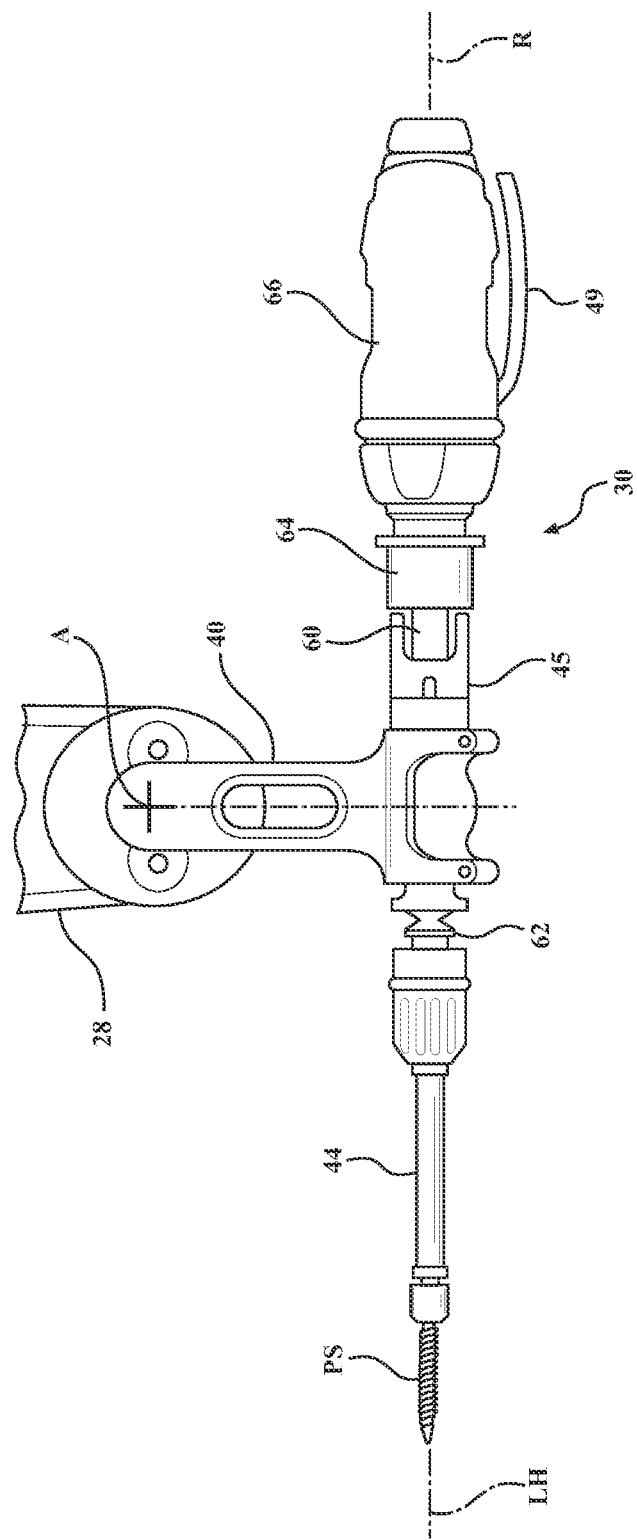
FIG. 6 is an elevational view of an alternative surgical tool.

In another embodiment shown in FIG. 6, one end of the coupling 40 supports the surgical tool 30 for rotation about the axis A. Another end of the coupling 40 supports the housing 45. The housing 45 may be fixed to the coupling 40 or may be supported for rotation within the coupling 40 about the rotational axis R. In other words, the housing 45 may be able to passively rotate within the coupling 40. At the same time, however, the coupling 40 limits axial movement of the housing 45 along the rotational axis R relative to the coupling 40 so that positioning of the housing 45 can be precisely controlled. A tracker (not shown) could be mounted to the housing 45 to track the position and/or orientation of the housing 45 and thereby track the rotational axis R and/or a distal end of the accessory attached to the housing 45. A rotating shaft 60 is rotatably supported in the housing 45. The rotating shaft 60 has a distal interface/collet 62 that couples to the accessory (e.g., driver 44 as shown) and a proximal interface/collet 64 that couples to a power source, such as a source of torque, e.g., a motor, rotatable handle for manual rotation, and the like. For example, the driver 44 is shown coupled to the distal interface 62/rotating shaft 60 and a handpiece 66 with internal motor is shown coupled to the proximal interface 64 so that the user is able to grip the handpiece 66, trigger operation of the motor, and cause the motor to transmit torque through the rotating shaft 60 to the driver 44 and ultimately to the pedicle screw PS. By virtue of this configuration, the user is able to feel direct torque feedback when inserting the pedicle screws PS.

Pre-operative imaging and/or intra-operative imaging may be employed to visualize the patient's anatomy that requires treatment—such as the patient's spine. The surgeon plans where to place the pedicle screws PS with respect to the images and/or with respect to a 3-D model created from the images. Planning includes determining a pose of each pedicle screw PS with respect to the particular vertebra V in which they are being placed, e.g., by identifying the desired pose in the images and/or the 3-D model. This may include creating or positioning a separate 3-D model of the pedicle screw PS with respect to the 3-D model of the patient's anatomy. Once the plan is set, then the plan is transferred to the robotic system 10 for execution.

The robotic system 10 may be used in concert with an imaging device 50 (e.g., a C-arm as shown in FIG. 3) to take the intra-operative images of the patient's anatomy in addition to, or alternatively to, any pre-operative images, e.g., X-rays, CT scans, or MRI images taken before surgery. The intra-operative images from the imaging device 50 can help to determine the actual position of the drill 42 or driver 44 relative to the desired orientation of the pedicle screws PS being placed in the patient's spine. Separate tracking devices 16 can be employed on each vertebra V to separately track each vertebra V and the corresponding pose of the drill 42 and/or driver 44 relative to the separate vertebra V when placing the pedicle screws PS or other implants into the vertebra V.

The robotic system 10 evaluates the desired pose of the pedicle screws PS and creates virtual boundaries (e.g., haptic objects), pre-defined tool paths, and/or other autonomous movement instructions, that correspond to the desired pose of the pedicle screws PS to control movement of the robotic arm 20 so that the drill 42 and driver 44 of the surgical tool 30 are controlled in a manner that ultimately places the pedicle screws PS according to the user's plan. This may comprise, for example, ensuring during the surgical procedure that a trajectory of the surgical tool 30 is aligned with the desired pose of the pedicle screws PS, e.g., aligning the rotational axis R with the desired pose of the pedicle screw PS.

In other embodiments, the user may intra-operatively plan the desired trajectory and/or screw placement. For example, the user can position the drill 42 at a desired entry point relative to the anatomy of interest, e.g., a vertebra V, and orient the drill 42 until the display 18 shows that the trajectory of the rotational axis R is in a desired orientation. Once the user is satisfied with the trajectory, the user can provide input (e.g., touchscreen, button, foot pedal, etc.) to the control system to set this trajectory as the desired trajectory to be maintained during the procedure. The haptic object created for constraining movement of the surgical tool 30 to maintain the rotational axis R to stay along the desired trajectory may be a line haptic object LH, such as that shown in FIG. 4. The line haptic object LH may have a starting point SP, as described further below, a target point TP, which defines a desired depth of the drill 42, pedicle screw PS, etc., and an exit point EP. Other haptic object shapes, sizes, etc. are also contemplated.

Figure 7:
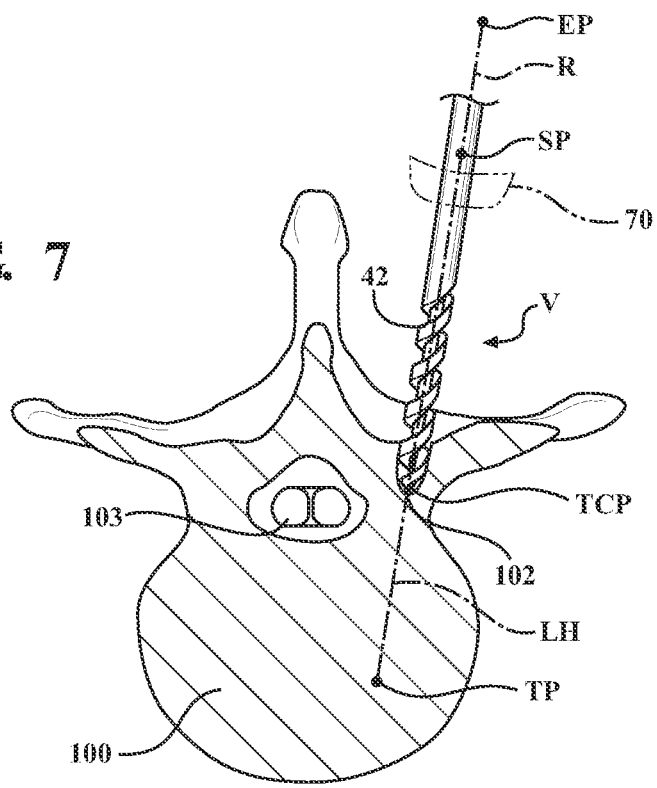
FIG. 7 is an illustration of drilling a pilot hole in a pedicle.
Figure 8:
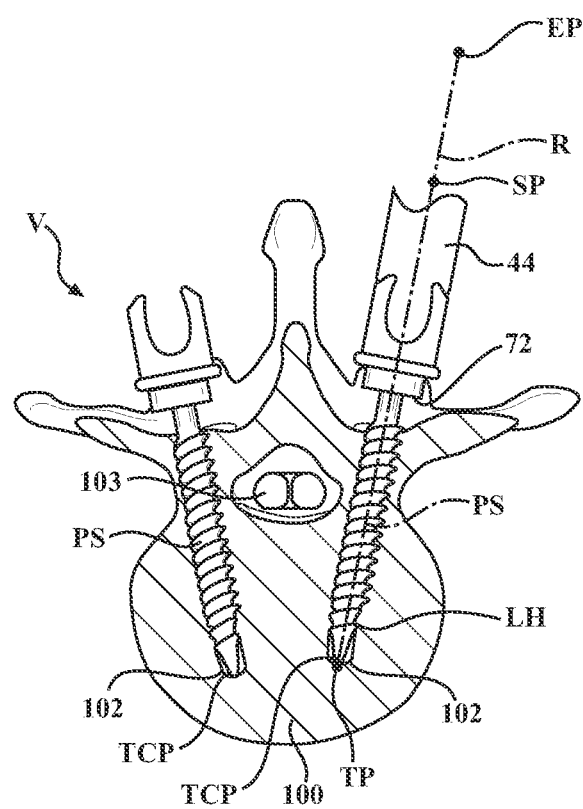
FIG. 8 is an illustration of driving a pedicle screw into the pilot hole.

Referring to FIGS. 7 and 8, one of the vertebra V is shown. During the surgical procedure, such as a spinal fusion surgery, a surgeon may insert one or more pedicle screws PS through pedicle regions into a vertebral body 100 of vertebra V. Prior to inserting the pedicle screws PS, the surgeon may employ the drill 42 to cut pilot holes 102 in the vertebral body 100. In an alternative embodiment, pilot holes may be excluded, such as where a self-drilling, self-tapping bone screw is employed. See, for example, the teachings in U.S. Pat. No. 7,637,929 to Stefan Auth, issued on Dec. 29, 2009, entitled "Self-drilling bone screw," which is hereby incorporated by reference herein in its entirety.

In one embodiment, before drilling commences, the robotic system 10 controls movement of the surgical tool 30 to place the rotational axis R along the desired trajectory by autonomously aligning the rotational axis R of the surgical tool 30 with the desired trajectory, which coincides with the desired orientation of the pilot holes 102. In this case, the robotic arm 20 may autonomously position the drill 42 along the desired trajectory, but spaced above the vertebral body 100 (as shown in FIG. 4) so that the drill 42 has not yet contacted the vertebral body 100. Such autonomous positioning may be initiated by the user pulling the trigger on the surgical tool 30, or otherwise providing input to the control system to start the movement. In some cases, a tool center point (TCP) of the surgical tool 30 is first brought to within a predefined distance of the starting point SP of the line haptic object LH that provides the desired trajectory (such as within a predefined starting sphere). Once the TCP (e.g., bur centroid, drill tip center, etc.) is within the predefined distance of the starting point SP, then pulling the trigger (or alternatively pressing a foot pedal or actuating some other input) causes the robotic arm 20 to autonomously align and position the surgical tool 30 on the desired trajectory. See, for example, the teachings in U.S. Patent Application Publication No. 2014/0180290 to Otto et al., filed on Dec. 21, 2012, entitled "Systems And Methods For Haptic Control Of A Surgical Tool," which is hereby incorporated by reference herein in its entirety. The robotic arm 20 may be programmed to move the surgical tool 30 to a distance from the patient based on pre-surgical planning or may move the TCP to the closest point on the trajectory. Once the surgical tool 30 is in the desired pose, the robotic system 10 may effectively hold the rotational axis R of the surgical tool 30 on the desired trajectory by tracking movement of the patient and autonomously adjusting the robotic arm 20 as needed to keep the rotational axis R on the desired trajectory, i.e., aligned with the line haptic object LH.

While the robotic system 10 holds the surgical tool 30 on the desired trajectory, the user may then manually manipulate the surgical tool 30 to move (or cause movement of) the drill 42 along the line haptic object LH toward the vertebral body 100 to drill the pilot holes 102. In some cases, such as when using a passive robotic arm 20, the robotic system 10 constrains the user's movement of the surgical tool 30 to stay along the desired trajectory by providing haptic feedback to the user should the user attempt to move the surgical tool 30 in a manner that deviates from the line haptic object LH and the desired trajectory. If the user desires to return the robotic arm 20 to a free mode, for unconstrained movement of the surgical tool 30, the user can pull the surgical tool 30 back along the line haptic object LH, away from the patient, until the exit point EP is reached.

The user then drills the pilot holes 102 to desired depths. Drilling speed can be controlled by the user via the trigger, or can be controlled automatically based on the particular location of the drill 42 relative to the patient's anatomy. For instance, a rotational speed of the drill 42 may be set high during initial drilling into the vertebral body V, but may be slowed during further drilling into the vertebral body V, and set even slower during final drilling to the final depth. The control system can also monitor contact/contact force during line haptic guiding via one or more sensors S (e.g., one or more force sensors, force/torque sensors, torque sensors, pressure sensors, optical sensors, or the like) that communicates with the robotic controller 32. If no significant contact/contact force is detected, which means the surgical tool 30 is passing through soft tissue, the control system avoids activating the motor of the surgical tool 30 or other power source (e.g., RF energy, ultrasonic motor, etc.). When contact with bone is detected (e.g., optically, sensed force is above a predefined threshold, etc.), the control system can activate the motor or other power source. Users can also passively feel the contact/contact force and trigger a switch to activate the power source.

The virtual boundaries (e.g., haptic objects) used to constrain the user's movement along the desired trajectory may also indicate, via haptic feedback, when the user has reach the desired depth of the pilot holes 102, e.g., reached the target point TP. Separate virtual boundaries could also be used to set the desired depths. In other cases, the robotic system 10 may autonomously drill the pilot holes 102 to the desired depths. In further cases, the robotic system may initially drill autonomously, but then final drilling may be done manually, or vice versa. Once the pilot holes 102 are created, the pedicle screws PS can then be placed using the driver 44. In some embodiments, pilot holes 102 may be unnecessary and the pedicle screws PS can be placed over guide wires placed by the robotic system 10 or without any guidance. Pilot holes may be unnecessary, such as where a self-drilling, self-tapping bone screw is employed. See, for example, the teachings in U.S. Pat. No. 7,637,929 to Stefan Auth, issued on Dec. 29, 2009, entitled "Self-drilling bone screw," which is hereby incorporated by reference herein in its entirety.

One advantage of using the navigation system 12 to continuously track each vertebra V separately and to track movement of the drill 42 is that the pedicle screws PS may be inserted in close proximity to spinal cord 103, and thus, the placement of pedicle screws PS and their corresponding pilot holes 102 must be precisely aligned so as to avoid interacting with or damaging spinal cord 103. If a surgeon drills the pilot holes 102 at an improper angle and/or too deeply, pedicle screws PS or the drill 42 used to drill pilot holes 102 may damage the spinal cord 103. As a result, by using the navigation system 12 to track a pose of the drill 42 and/or the driver 44 relative to the patient's anatomy and specifically the anatomy as outlined in the preoperative images and/or the intraoperative images, the spinal cord 103 can be avoided.

Once drilling is complete, referring specifically to FIG. 7, the drill 42 is removed from the vertebral body 100, the drill 42 is disconnected from the drive system via the collet 47, and the driver 44 is coupled to the drive system (with or without the speed reducer 48). A pedicle screw PS is attached to a distal end of the driver 44 for placement in one of the pilot holes 102. The original line haptic object could be used for driving the pedicle screw PS or a new line haptic object, with new starting point, target point, and exit point, could be created upon attaching the driver 44 and/or pedicle screw PS. In this case, the drill 42 and/or driver 44 could have RFID tags or other identification devices so that the robotic controller 32 is able to identify which accessory is connected to the housing 45. The housing 45 may have a corresponding RFID reader, etc. in communication with the robotic controller 32 to read the tag and determine which accessory is attached. Based on this information, the controller may then create, access, or otherwise determine a new line haptic object. Similarly, the pedicle screws PS could also be outfitted with RFID tags and the driver 44 may have a similar reader so that the robotic controller 32 can also determine which size/type of pedicle screw PS is attached. Accordingly, the line haptic object can be based on the driver 44 and/or the pedicle screw PS so that the robotic arm 20 is controlled precisely to place that particular pedicle screw PS to a desired location, e.g., a desired orientation and depth with respect to the patient's anatomy.

Additionally, with automatic detection of the accessory, either via the RFID tags, or other detection devices, such as a vision camera, the control system is able to advance any surgical procedure software utilized with the robotic system 10 to the next screen associated with the driver 44, which may have different prompts, instructions, etc. for the user now that the driver 44 is connected. Voice recognition, gesture sensing, or other input devices may be used to advance the software and/or to change to the next vertebra 100 to be treated and/or to change a side of the vertebral body 100 in which the operation is being carried out. This could also be based on the location of the surgical tool 30. For example, if the TCP of the attached accessory is manually placed by the user closer to one side of a particular vertebra V than another, the software may automatically advance to correspond to that side of the vertebra V. The selected vertebra V and side of operation can be confirmed visually with the displays 18 or through audio input/output.

Again, in much the same manner as the drill 42 is controlled, while the robotic system 10 holds the surgical tool 30 on the desired trajectory, the user may then manually manipulate the surgical tool 30 to move (or cause movement of) the driver 44 and pedicle screw PS along the line haptic object LH toward the vertebral body 100 to insert the pedicle screw PS in the pilot hole 102. In some cases, such as when using a passive robotic arm 20, the robotic system controls movement of the surgical tool 30 by constraining the user's movement of the surgical tool 30 so that the surgical tool 30 remains aligned with and stays along the desired trajectory. This can be accomplished by providing haptic feedback to the user should the user attempt to move the surgical tool 30 in a manner that deviates from the desired trajectory—thus the robotic arm 20 is still able to control installation of the implant in the spine of the patient so that the implant is placed at a desired location. The user then drives the pedicle screw PS into the pilot hole 102 to the desired location, e.g., to the desired depth at the desired orientation. Drive speed can be controlled by the user via the trigger, or can be controlled automatically based on the particular location of the driver 44 and/or pedicle screw PS relative to the patient's anatomy. For instance, a rotational speed of the driver 44 may be set high during initial installation into the vertebral body V, but may be slowed during further installation into the vertebral body V, and set even slower during final implanting to the final depth.

The virtual boundaries (e.g., line haptic objects) used to constrain the user's movement along the desired trajectory may also indicate, via haptic feedback, when the user has reach the desired depth of the pedicle screw PS. Separate virtual boundaries could also be used to set the desired depth. In other cases, the robotic system 10 may autonomously insert the pedicle screws PS to the desired depths. In further cases, the robotic system 10 may initially drive the pedicle screws PS autonomously to an initial depth, but then final implanting to a final depth may be done manually, or vice versa. In one example, the pedicle screws PS are placed autonomously until within a predefined distance of the final depth (as determined by the navigation system 12). At this point, the user either finishes implanting the pedicle screw PS manually with the surgical tool 30 so that the user is able to feel tightening of the pedicle screws 30, or a separate tool (powered or manual) is used to complete placement of the pedicle screw PS. The user may be instructed by the control system, via displays 18, how many turns remain before the pedicle screw PS has reached full depth, and/or the displays 18 may graphically represent the pedicle screws PS, anatomy, and/or the target point so that the user is able to easily visualize how much further driving of the pedicle screw PS is required.

In some procedures, the rotational axis R may be moved off the desired trajectory between drilling the pilot holes and driving the implants, such as when all the pilot holes are drilled first, and then later, all the pedicle screws PS are driven into their desired location. In such a case, before placing each of the pedicle screws PS, the robotic system 10 may first control movement of the surgical tool 30 to place the rotational axis R along the desired trajectory by autonomously aligning the rotational axis R of the surgical tool 30 with the desired trajectory for each of the pedicle screws PS in the manner previously described.

Figure 14:
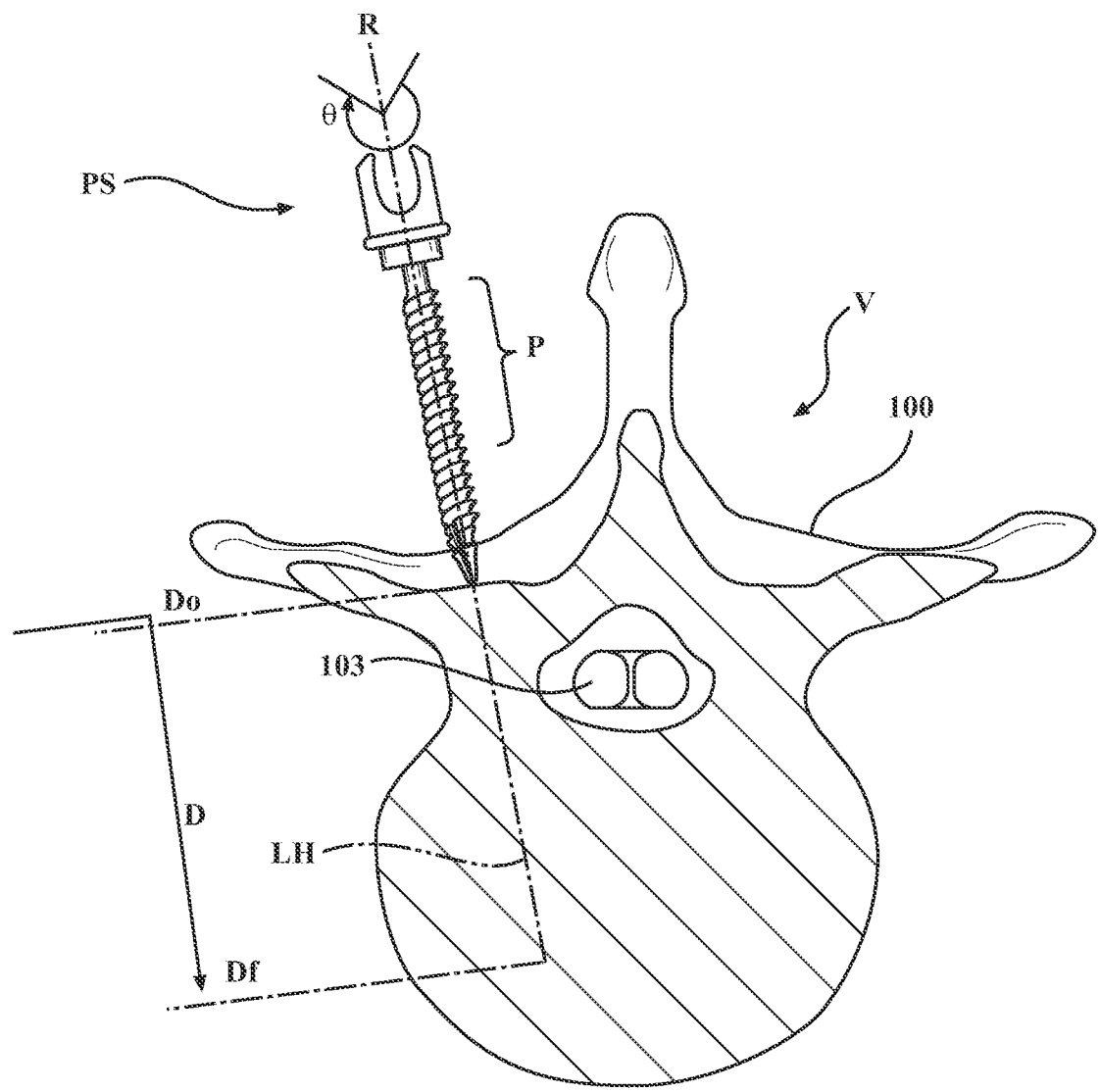
FIG. 14 is an illustration of driving a pedicle screw into the pilot hole.

In one alternative, the pedicle screws PS are inserted with assistance of the robotic system 10, where the robotic controller 32 controls the insertion such that the rotation speed about the rotational axis R and the rate of advancement along the planned trajectory are proportional to the thread geometry of the pedicle screw. For example, the thread geometry may include any one or more of pedicle screw PS length, thread diameter, depth of thread, head size, and thread pitch P. FIG. 14 illustrates a starting position of a pedicle screw PS adjacent to the target site, in this case, shown as vertebra V, with the planned trajectory designated by a linear haptic object LH. The threaded interface between the pedicle screw PS and the vertebral body 100 risks damage to the bone, the screw PS, the driver 44 or surgical tool 30 if the pedicle screw is inserted incorrectly. The bone is likely the weakest material and thus most likely to suffer damage if the screw is inserted incorrectly. Improper insertion may occur, for example, when the pedicle screw PS advances linearly along the trajectory LH with insufficient rotation about the rotational axis R. This may cause bone material to shear off adjacent to the threads and be forced down into the bone. In another example, improper insertion may occur when, for example, the pedicle screw PS is rotated about the rotational axis R with insufficient advancement along the trajectory LH, causing bone material to shear off adjacent to the threads and be forced back along the threads, in effect over drilling the hole. In either example, the result of the improper insertion is to decrease the strength and amount of bone material to secure the pedicle screw PS in the bone.

FIG. 14 illustrates the pedicle screw PS at a starting point Do adjacent to the vertebral body 100 for insertion using position control to address this potential risk. Position control for inserting a screw ensures that the proper depth position and angular or rotational position are maintained throughout the operation. The vertebral body 100 may be prepared with a pilot hole, as shown in the embodiments above, or the operation may employ a self-drilling and self-tapping screw so that no pilot hole is required. The starting point Do of the pedicle screw PS is adjacent to the vertebral body 100, that is, prior to any part of the screw penetrating into the vertebral body 100. In an alternative, the starting point Do may be spaced away from the vertebral body 100 by a distance as a safety margin to ensure proper position control throughout the operation. The depth of insertion D advances along the trajectory LH to a final depth Df as the planned depth to complete installation of the pedicle screw 100 in the vertebral body 100.

The robotic controller 32 is configured to control the insertion of the pedicle screw PS so that the rotational speed and the rate of advancement along the trajectory LH are proportional to the thread pitch P of the pedicle screw PS. The pedicle screw PS has a known geometry and is presented virtually within the navigation system 12. Thread pitch P is defined as the number of treads per unit length. In specific example, the pedicle screw illustrated in FIG. 14 may have a thread pitch of 12 threads per inch. Other exemplary pedicle screws PS may have 8, 10, 14, 16 or other number of threads per inch. Having a defined relationship between the robotic arm 20 and the pedicle screw PS, and a known geometry of the pedicle screw PS stored in the memory of the robotic system 10, the robotic controller 32 is configured to ensure to proper rotational speed and advancement speed for inserting a pedicle screw having a particular thread pitch.

The thread geometry of the pedicle screw PS can be stored in memory of the robotic system 10 pre-operatively or intraoperatively. In one example, the pedicle screw PS is chosen as part of a surgical plan, and the corresponding thread geometry of the pedicle screw PS is associated with the pedicle screw PS and inputted into the plan. Once the plan is loaded for intraoperative surgery, the robotic system 10 will have the known the thread geometry stored in memory for immediate access. In another example, the operator can manually select different pedicle screws PS, or can manually input the thread geometry using a GUI affiliated with operation of the robotic system 10. The inputted thread geometry may be obtained from a database stored in memory, or can be derived from the operator obtaining such information from offline specifications associated with a chosen pedicle screw PS. In any of these examples, the thread geometry can be stored in memory after the operator input using GUI such that the robotic system 10 can subsequently carry out the control techniques described herein with the inputted thread geometry. In yet another example, a measurement tool directly or wirelessly connected to the robotic system 10 may be utilized to scan or measure any intended pedicle screw PS to extract the thread geometry and transmit the measured thread geometry to the robotic system 10 memory.

The relationship between the pedicle screw thread pitch, the angular, or rotational, position and the depth of insertion, or advancement along the trajectory, is governed by the equation $\theta = D*(Pitch/2\pi)$, where $\theta$ is the angular position, D is the depth of insertion in unit length, Pitch is the threads per unit length of the pedicle screw PS. The robotic controller 32 uses this relationship to control the installation of the pedicle screw. For example, taking the first derivative with request to time, the rate of change in angular position, or rotation speed, $\delta\theta/\delta t$, is equal to the rate of change in depth of insertion, or advancement rate, $\delta D/\delta t$, multiplied by the Pitch divided by $2\pi$. This can be expressed as:

$$\frac{\delta\theta}{\delta t} = \frac{\delta D}{\delta t} * \frac{Pitch}{2\pi}. \qquad (Eq. 1)$$

As described above, the robotic arm may operate in an active manner, where the user applies a force to the surgical tool, which is measured by a force/torque sensor. The robotic arm emulates the user's desired movement based on the measurement from the force/torque sensor. The robotic controller 32 may be configured to command a displacement of the robotic arm 20 in the direction of the applied force, and proportional to the magnitude of the applied force. The robotic controller 32 is further configured to maintain the proportional relationship between the rotation speed and the advancement rate of the pedicle screw PS relative to the thread pitch.

Figure 15:
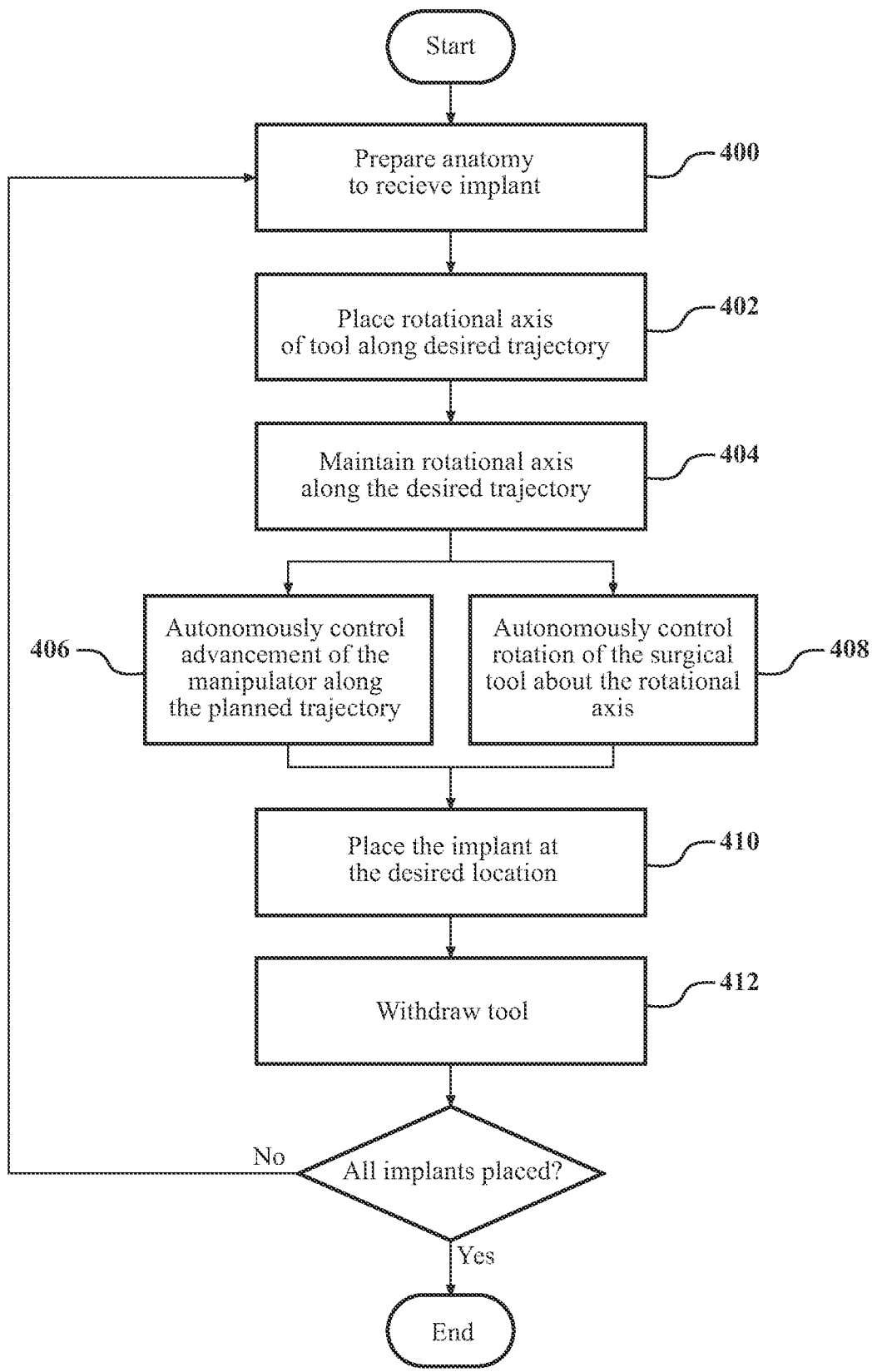
FIG. 15 is a flow chart of sample steps carried out in one procedure to place an implant at a desired location.

In one alternative, as illustrated in FIG. 15, a method of placing an implant is provided. FIG. 15 illustrates a flowchart of sample steps that could be carried out in a surgical procedure for placing an implant at a desired location, such as placing a screw into a bone. In step 400, the anatomy is first prepared to receive the implant. Such preparation may comprise several steps, such as: (1) forming an incision in the patient (see also, FIG. 13); (2) retracting tissue with a retractor; (3) drilling a pilot hole in the anatomy; (4) tapping treads into the anatomy; and the like. Not all preparation steps need be performed in all operations. For example, where a self-drilling, self-tapping screw is employed, no separate preparatory steps of drilling a pilot hole, or tapping threads in necessary.

If the rotational axis R is not yet aligned with the planned trajectory LH, as in FIG. 14, according to the surgical plan, or if the rotational axis R has been move away from the desired trajectory for other reasons, the rotational axis R is aligned in step 402. Specifically, in step 402, the robotic system 10 controls movement of the surgical tool 30, to place the rotational axis R along the desired trajectory. This may comprise the robotic system 10 causing autonomous movement of the surgical tool 30, to place the rotational axis R along the desired trajectory. Alternatively, the robotic system 10 may enable the user to move the surgical tool 30 by applying force/torque in a manual mode until the rotational axis R is placed along the planned trajectory LH. The robotic system 10 can generate feedback (visual, audible, and/or haptic) to the user to indicate proper alignment. In some examples, attractive haptics may be utilized to pull the tool 30 toward the planned trajectory LH as the position of the tool is near the planned trajectory LH by a threshold distance defined by the attractive haptics.

Once the rotational axis R has been placed on the desired trajectory, then the robotic system 10 operates to maintain the rotational axis R along the desired trajectory in step 404. This may comprise constraining movement, whether autonomous or manual, of the surgical tool 30, so that the surgical tool 30, remains aligned with the desired trajectory during the entirety of the operation until the implant has been placed at the desired location.

Installation of the implant in the vertebra V of the patient occurs in steps 406-410, such that the implant is placed at the desired location. In steps 406 and 408, the robotic system 10 causes autonomous movement of the surgical tool 30, to simultaneously control the autonomous advancement of the tool linearly along the planned trajectory, while also controlling the autonomous rotation of the surgical tool about the rotational axis R. The autonomous control of the advancement and the rotation is related to the thread pitch defined by the equation Eq. 1, described above. The autonomous control dictated by the thread pitch ensures proper installation of the pedicle screw to avoid causing damage to surrounding bone tissue.

The autonomous control continues through the completion of step 410, where the robotic system 10 places the implant at the desired location, that is, at the ultimate insertion depth according to the surgical plan.

The step 400-410 can be commanded by the user in multiple alternatives. In a first example, the robotic system 10 may be configured to execute in complete autonomy. That is, once the user has commanded the robotic system 10 to perform the operation, the robotic system 10 performs the operation with no further user input until the operation completes. In an alternative embodiment, the user may initiate the autonomous execution of the operation and then provide the continuing input such as by pressing and holding a button, by pressing and holding a foot switch, or other continuous input control so that if the input ceases, e.g. the button or footswitch is released, then the robotic system 10 pauses execution of the operation. In cooperation with the autonomous control, the user may modulate the speed at which the operation executes. In addition to a button or footswitch, an additional control may be provided so that the user can command an increase or decrease in the robot speed in a step-wise function with multiple discrete speeds. The additional speed control, may include a set of buttons, selectors, dials, or other suitable control.

In a further embodiment, the method includes using the robotic system 10 in an active manner where the user applies a force to the surgical tool, which is measured by a force/torque sensor. The robotic system emulates the user's desired movement of the robotic arm based on the measurements from the force/torque sensor. In this embodiment, the user may toggle the robotic system into an autonomous mode, and command the execution of the autonomous control operation for inserting the implant. The robotic system 10 receives a signal from the force/torque sensor indicative of an input applied by the user and executes the autonomous control at a speed proportionate to the magnitude of the input force. The robotic system 10 may be further configured to pause execution of the operation if the user removes their hand from the control or otherwise fails to input any force to the force/torque sensor.

In a further embodiment, the method includes using the robotic system 10 including the surgical tool 30, shown in FIGS. 4-6, and having a trigger 49 which may communicate signals to the robotic controller 32 indicative of a user's input. The robotic system 10 may be configured to operate in a mode such that the user has control of either one of the rotational speed about the rotational axis R or the advancement along the trajectory during installation of the implant according to the amount the trigger 49 is depressed. In steps 406-410 the user provides an input by, for example, variably depressing the trigger 49 to control the rotational speed or the advancement rate. The robotic system responds to the input by controlling the other of the advancement rate or the rotational speed to maintain both aspects of the installation of the implant proportional to the thread pitch according to the relationship defined in equation Eq. 1, described above.

After step 410, with the implant placed at the desired location, at step 412 the tool is withdrawn from the implant. As with advancing the implant into the bone, the user may input a force at the surgical tool in the direction away from the vertebra V to command the withdrawal of the surgical tool. Alternatively, the robotic system 10 may autonomously withdraw the surgical tool without further input from the user once the implant is placed. The process as described at steps 400-412 may be performed anew to place an additional implant, and continue until all implants have been placed according to the surgical plan.

A partial facetectomy may be carried out with the surgical tool 30 to provide a smooth bony surface for final receipt of a head of the pedicle screw PS. The resection volume can be defined based on the user's plan, i.e., by determining a location of the head in the 3-D model. A bur or pre-shaped reamer 70 that corresponds to the head shape can be used to remove the material. In some cases, the drill 42 may incorporate the reamer therein, as shown in hidden lines in FIG. 7, to avoid separate tools so that the drill 42 has a smaller profile drilling shaft to create the pilot hole and more proximally located is the reamer 70 to create the seat 72 for the head of the pedicle screw PS—thus at least part of the pilot hole 102 and the seat 72 can be formed simultaneously. In the embodiment shown, the drill 42 has a drilling shaft with proximal and distal ends and a drill tip at the distal end. The reamer 70 is spaced proximally from the drill tip so that the reamer 70 is located near a facet once the drill 42 has been inserted to the desired depth in the target vertebral body. Any suitable drill and/or reamer cutting features may be employed to form the hole, e.g., to form the pilot hole and the seat in the spine of the patient to receive the implant.

The robotic controller 32 can be used to control insertion of the pedicle screws PS by measuring torque associated with driving of the pedicle screws PS with the driver 44. More specifically, the torque required to insert the pedicle screws PS into the vertebral body 100 increases the deeper the pedicle screw PS is placed in the vertebral body 100, and further increases once an end of the pilot hole 102 is reached. As a result, torque output of the motor in the surgical tool 30 can indicate whether the pedicle screw PS has reached the desired depth and/or the end of the pilot hole 102. The robotic controller 32 monitors this torque (e.g. via a torque sensor, such as by monitoring current draw of the motor, or the like) and controls rotation of the driver 44 accordingly. For instance, once a threshold torque is reached, the driver 44 may be stopped.

Figure 9A:
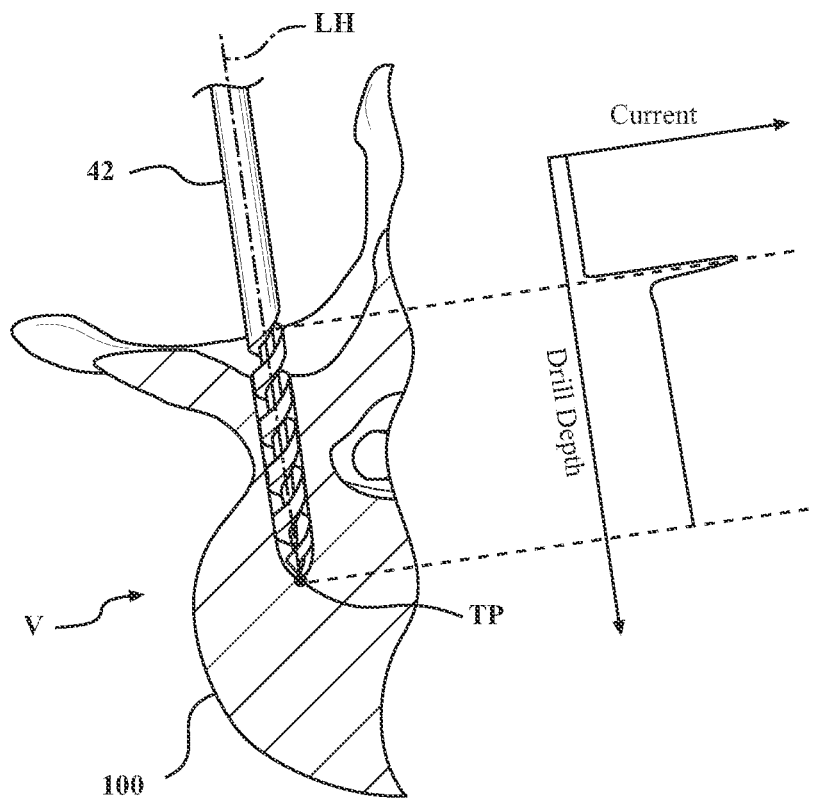
FIGS. 9A and 9B are illustrations showing electrical current output vs. depth, which can be used to verify that drilling and pedicle screw insertion is according to a user's plan.
Figure 9B:
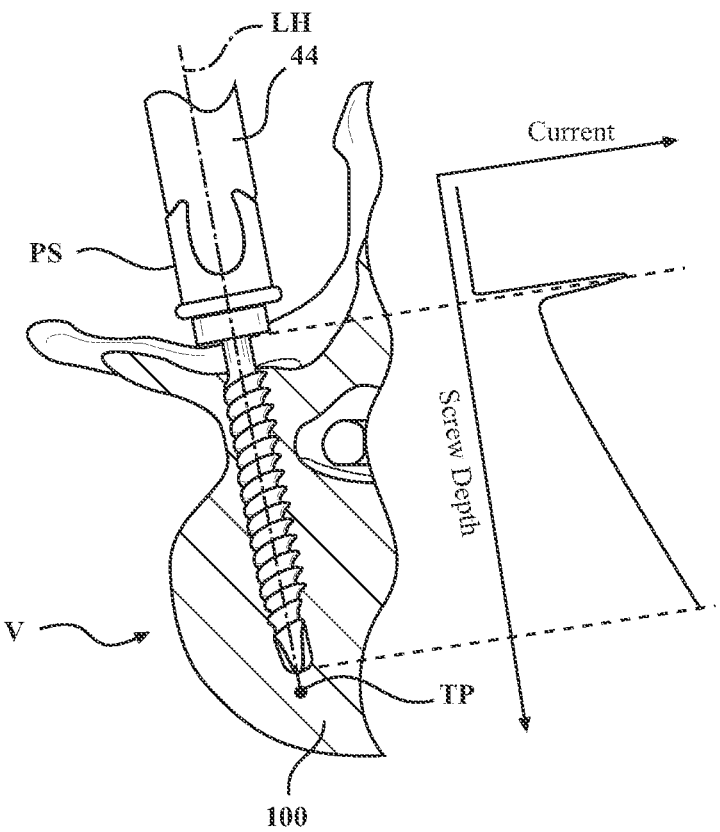

Referring to FIGS. 9A and 9B, the control system may also be able to use the torque output, e.g., current, or other measured force parameter to verify the location of the drill 42 or pedicle screw PS during insertion. This may be particularly useful in cases where the tracking device 16 inadvertently moves relative to the vertebra 100, which may otherwise be undetected and result in errors in drilling or screw driving. For example, pre-operative and/or intra-operative images taken of the vertebra 100 may be used to generate a volumetric map of bone mineral density (BMD) for the vertebra 100. Generating and utilizing such BMD maps for robotic surgery is shown and described in U.S. Patent Application Publication No. 2017/0000572 to Moctezuma de la Barrera et al., filed on Jun. 28, 2016, entitled "Robotic Systems And Methods For Controlling A Tool Removing Material From A Workpiece," which is hereby incorporated by reference herein. During the drilling or screw driving, the control system can evaluate the BMD map to predict the BMD at the contact point of the drill 42/pedicle screw PS with the bone according to the 3-D model and the user's plan (i.e., the current contact point if the drill/pedicle screw PS is following the plan). The control system can then predict the corresponding value of current or torque of the surgical tool 30 or interaction force (e.g., using a force/torque sensor) and compare its value to measured actual values to determine if a discrepancy above a threshold is found. If a discrepancy is found, it can be used to stop the procedure or update the plan. FIG. 9B illustrates a profile of insertion current, torque, and force of pedicle screws PS. In effect, during screw driving, the robotic system 10 can monitor the profile of insertion current, torque, and force of screws to indicate that the pedicle screw follows the planned trajectory. The profile of insertion torque can also be used to indicate a degree of osteoporosis of bone.

An ultrasound transducer (not shown) could also be mounted on the back of the patient's skin to generate real-time images of the patient's anatomy and progress of the surgical procedure. The intra-operative images could be used to determine that the pedicle screw PS follows the planned desired trajectory or to determine if the drill 42 or pedicle screw PS, is getting close to any critical structures including a nerve and medial or lateral cortical boundary.

Figure 10A:
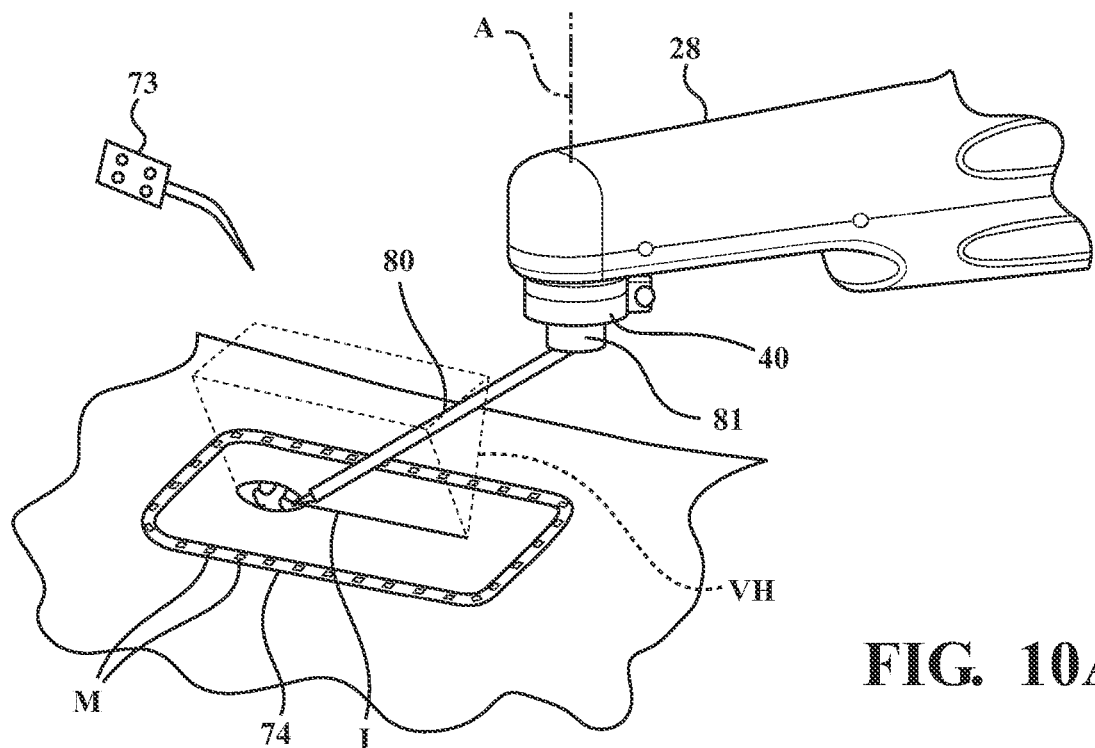
FIG. 10A is an illustration of a skin incision tool attached to the robotic arm.

Referring to FIG. 10A, one of the accessories of the surgical tool 30 may comprise a skin incision tool 80, such as a scalpel, electrosurgical knife, other tools with sharp tips, and the like. The skin incision tool 80 can be mounted much like the drill 42 and/or driver 44, or may be part of a separate end effector and connected to a mount 81 that attaches to the coupling 40, and a skin incision I can be made with haptic guidance in a similar manner as previously described, i.e., virtual boundaries (e.g., haptic objects) can be used when creating the incision I to constrain the user's movement with respect to a desired incision in the patient's skin. In one example, the digitizing probe 73 can be used to touch the desired incision location and create the associated boundary/haptic object. In another example, a 3-D skin model can be determined based on the pose of the ring 74, through digitizing, and/or through pre-operative methods, and the desired plan of pedicle screw placement can be used by the control system to determine the incision I location based on the skin model.

Figure 10B:
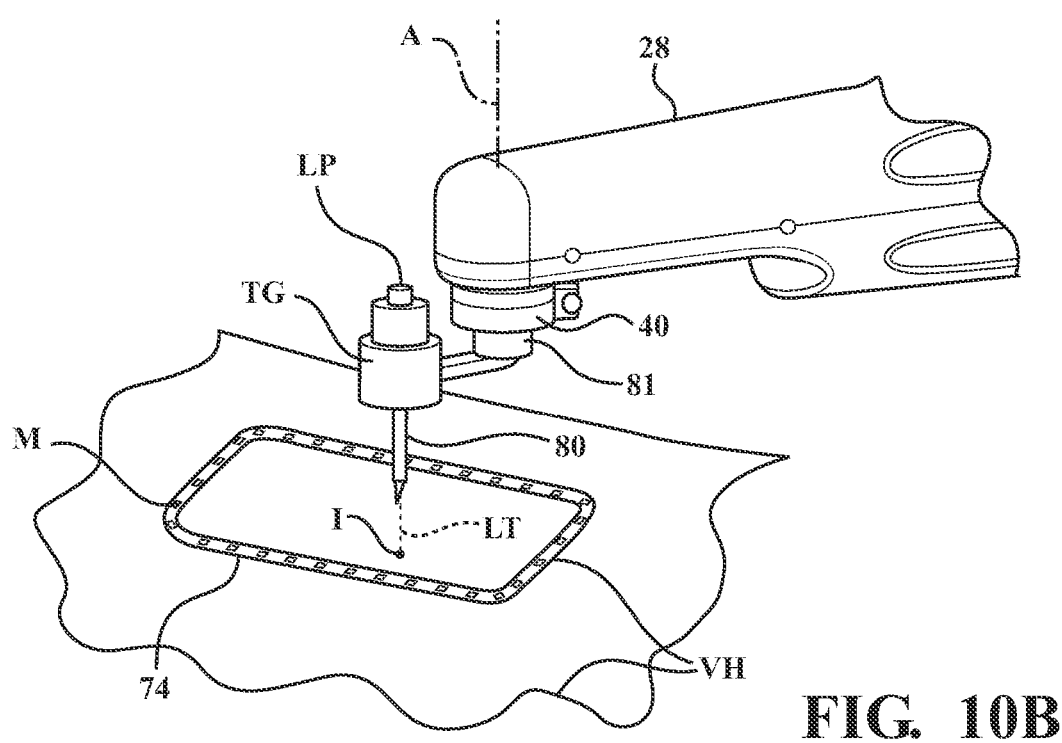
FIG. 10B is an illustration of an alternative skin incision tool attached to the robotic arm.

Referring to FIG. 10B, other types of pointers, similar to the digitizing probe 73 can also be used to identify the desired location of the incision, such as a laser pointer LP that could be mounted to the skin incision tool 80, end effector, or other component to project visible light LT onto the skin of the patient to indicate the location of the incision. Such a laser pointer can be used by first aligning the rotational axis R of the skin incision tool 80 with the desired trajectory and thereafter activating the laser pointer LP to project the light along the desired trajectory. An alternative form of skin incision tool 80 is shown in FIG. 10B, which is placed through a tool guide TG held in place by the robotic arm. Owing to the tracking of the patient's skin accomplished via the skin tracker (e.g., the ring 74), the navigation system 12 is also able to approximately determine the desired location of the incision I based on the skin model (e.g., a surface model, point cloud, etc.) and the intersection of the desired trajectory with the skin model so that the user is able to cut the desired incision in the patient's skin at the desired location by virtue of haptic feedback.

Haptic objects can be defined in various ways to establish the haptic feedback to guide making of the incision (see, e.g., the V-shaped haptic object VH shown in FIG. 10A). The haptic objects can be defined based on a width of the skin incision tool, a desired length of the skin incision, and/or a desired depth of the incision. A desired incision depth can also be controlled by the user within a maximum incision depth which can be determined by either the maximum incision depth programmed as part of the haptic object or a mechanical stop can be used to prevent the skin incision tool 80 from sliding through a guide opening (not shown) in the tool guide TG of the end effector beyond a predetermined point.

Figure 11:
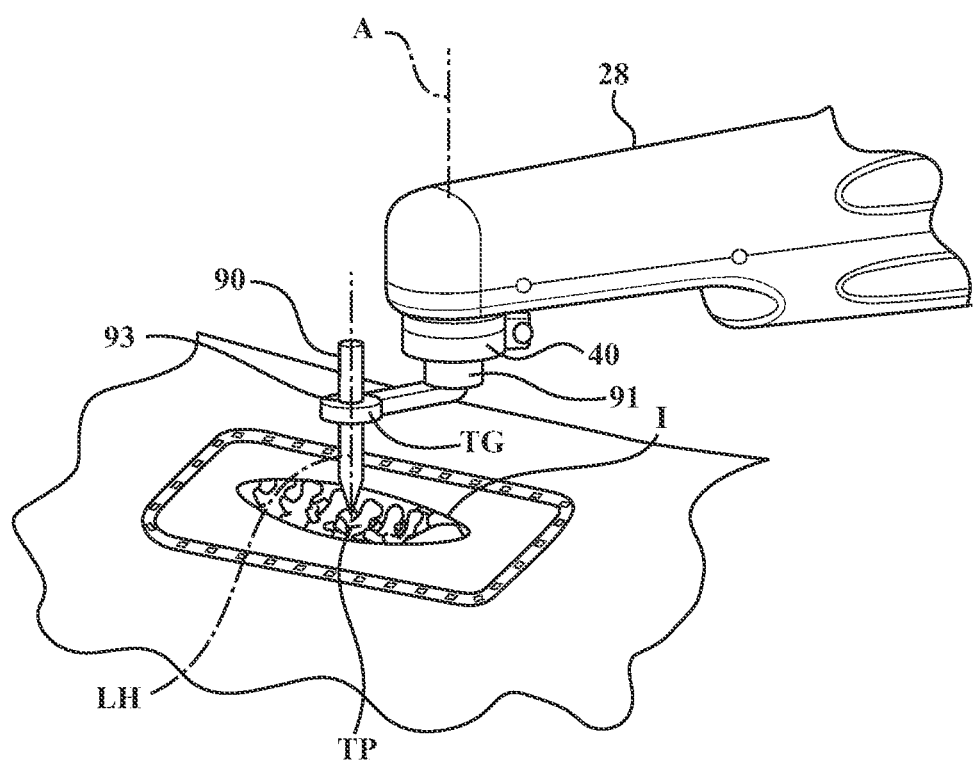
FIG. 11 is an illustration of a Jamshidi needle attached to the robotic arm.

Referring to FIG. 11, one of the accessories of the surgical tool 30 may comprise a wire insertion tool 90, such as a Jamshidi needle, another access cannula with stylet, or the like. The wire insertion tool 90 can be mounted much like the skin incision tool 80, or may be part of a separate end effector and fixedly connected to a mount 91 that attaches to the coupling 40. If no relative motion is allowed between the wire insertion tool 90 and the mount 91, i.e., they are fixed to one another, then the wire insertion tool 90 can be guided with a line haptic object LH to enter the skin incision I and reach a target point TP on the bone, e.g., the vertebra. If relative axial sliding motion between the wire insertion tool 90 and the mount 91 is allowed, such as when the mount 91 comprises a tool guide TG with opening 93, then the tool guide TG can be positioned at the desired orientation and the wire insertion tool 90 can be inserted along opening 93 in the tool guide TG. Depending on relative distance to the target point TP, length of the wire insertion tool 90, and the tool guide position, the wire insertion tool 90 can be guided via the line haptic object LH in the same manner previously described for the drill 42 and/or driver 44.

Figure 12:
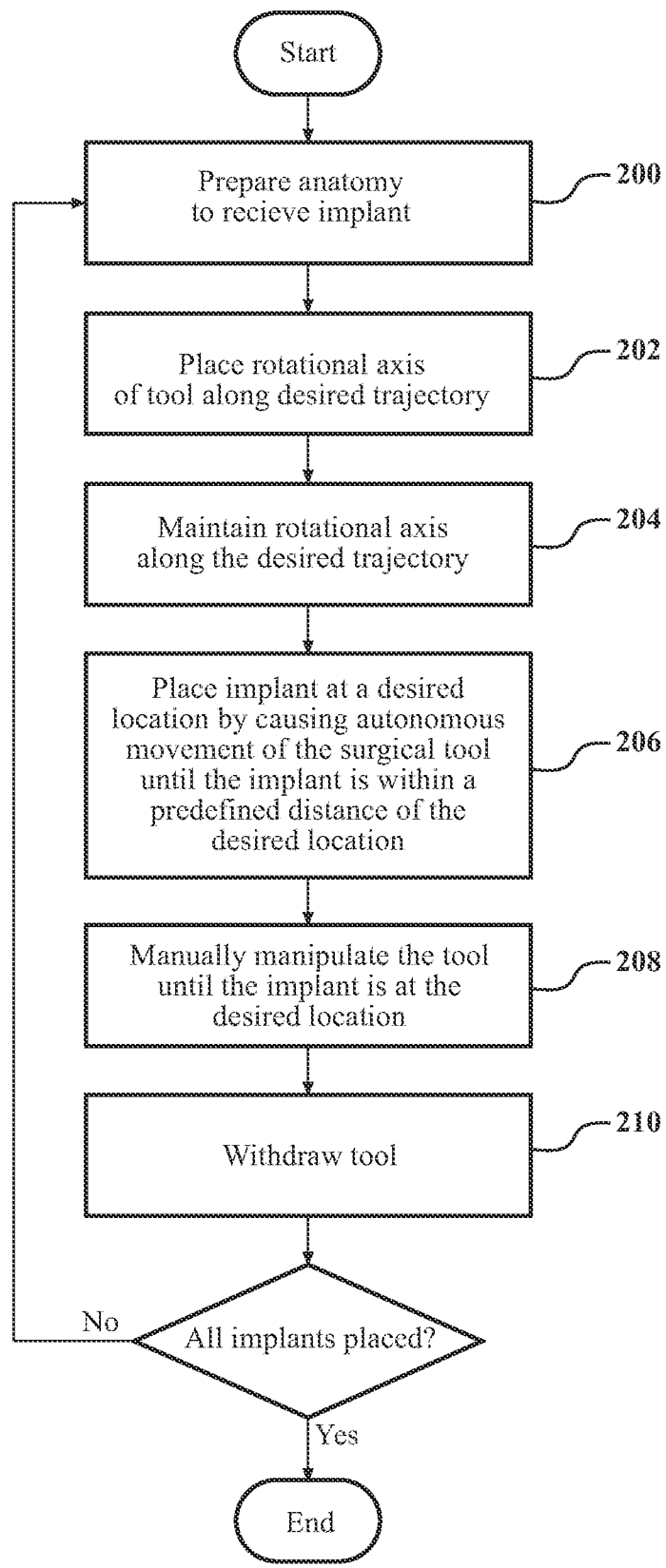
FIG. 12 is a flow chart of sample steps carried out in one procedure to place an implant at a desired location.

FIG. 12 illustrates a flowchart of sample steps that could be carried out in a surgical procedure for placing an implant at a desired location, such as placing a screw into bone. In step 200, the anatomy is first prepared to receive the implant. Such preparation may comprise several steps, such as: (1) forming an incision in the patient (see also FIG. 13); (2) retracting tissue with a tissue retractor; (3) placing a cannula in the retracted tissue; (4) drilling a pilot hole in the anatomy; (5) tapping threads into the anatomy; and the like.

If the rotational axis R is not yet aligned with the desired trajectory, or if the rotational axis R has been moved away from the desired trajectory for other reasons, the rotational axis R is aligned in step 202. Specifically, in step 202, the robotic system 10 controls movement of the surgical tool 30 to place the rotational axis R along the desired trajectory. This may comprise the robotic system 10 causing autonomous movement of the surgical tool 30 to place the rotational axis R along the desired trajectory.

Once the rotational axis R has been placed on the desired trajectory, then the robotic system 10 operates to maintain the rotational axis R along the desired trajectory in step 204. This may comprise controlling manual manipulation of the surgical tool 30 by constraining movement of the surgical tool 30 so that the surgical tool 30 remains aligned with the desired trajectory while a user manually moves or manually causes movement of the surgical tool 30 toward the spine.

Installation of the implant in the spine of the patient occurs in steps 206 and 208 such that the implant is placed at a desired location. In step 206, the robotic system 10 causes autonomous movement of the surgical tool 30 to place the implant in the spine of the patient until the implant is within a predefined distance of the desired location. Thereafter, in step 208 the user manual manipulates the surgical tool 30 and the robotic system 10 controls such manual manipulation of the surgical tool 30 until the implant is placed at the desired location. The robotic system 10 can control such manual manipulation, for instance, by generating haptic feedback to the user with the robotic controller 32 to indicate that the implant has reached the desired location. Once the implant is placed at the desired location, the surgical tool 30 is withdrawn away from the anatomy in step 210 and the procedure proceeds until all implants are placed.

Figure 13:
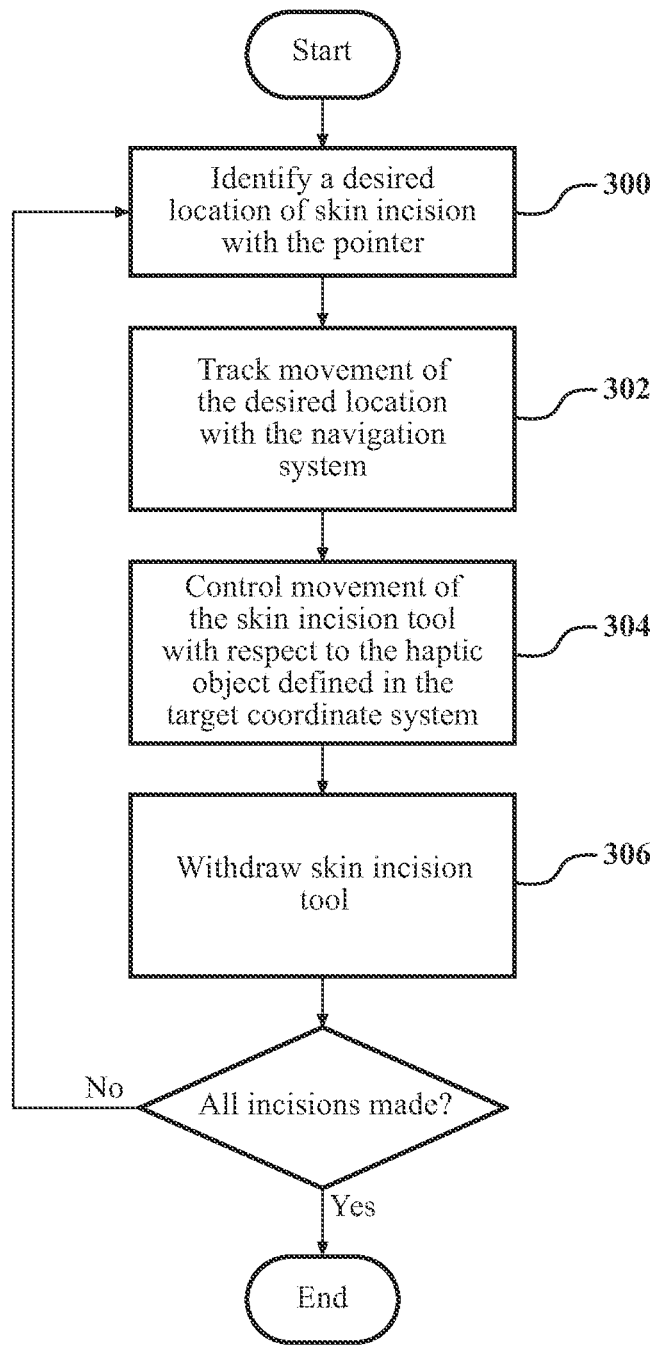
FIG. 13 is a flow chart of sample steps carried out in one procedure to make an incision.

FIG. 13 illustrates a flowchart of sample steps carried out to form the incision I in the skin of the patient. In step 300, a desired location of the incision is first identified with the pointer, while the skin tracker (e.g., ring 74) is attached to the patient. In one example, the pointer comprises the digitizing probe 73 which can be used to touch the desired incision location to identify the desired location of the incision I and create the associated boundary/haptic object. In another example, the laser pointer LP can be used to identify the desired location of the incision.

In step 302, once the desired location of the incision I is identified, then the skin (and the desired location on the skin for the incision I) can be tracked with the navigation system 12 in the manner previously described.

Owing to the skin and the desired location for the incision I being tracked, the robotic system 10 can control movement of the skin incision tool 80 with respect to a haptic object created for the incision in step 304. The haptic object is defined in the target coordinate system so that the incision is made at the desired location in the skin of the patient. In one example, the robotic system 10 can control movement of the skin incision tool 80 with respect to the haptic object by controlling manual manipulation of the skin incision tool 80. This can be done by constraining movement of the skin incision tool 80 with respect to a virtual boundary defined by the haptic object so that the skin incision tool 80 makes the incision I at the desired location while a user manually moves or manually causes movement of the skin incision tool 80. The robotic system 10 can constrain movement of the skin incision tool 80 with respect to the haptic object by generating haptic feedback to the user to indicate that the skin incision tool 80 has reached a desired depth of the incision I or otherwise has reached a desired limit for the incision I. Once the incision I is made at the desired location, the skin incision tool 80 is withdrawn away from the anatomy in step 306 and the procedure proceeds until all incisions are made.

It should be appreciated that the systems and methods described herein can be employed to place pedicle screws PS, other screws, fasteners, or other implants into a patient. So, even though pedicle screws PS are referenced throughout as one example, the same systems and methods described herein could be utilized for treating any anatomy of the patient and/or for placing any implants into the patient, e.g., in the hip, knee, femur, tibia, face, shoulder, spine, etc. For instance, the robotic arm 20 may also be used to place a cage for a spine implant, to place rods, or to place other components, and could be used for discectomy or other procedures. Different end effectors could also be attached to the robotic arm 30 for other procedures. In some cases, the end effector may also have an articulating arm to facilitate implant insertion, i.e., placing the implant in a desired pose. The articulating arm of the end effector could simply be a miniature version of the robotic arm 20 controlled in the same manner to place the implant or could be another mechanism controlled to position the implant. The navigation system 12 may comprise an optical navigation system with optical-based trackers, but could additionally or alternatively employ other modalities, such as ultrasound navigation systems that track objects via ultrasound, radio frequency navigation systems that track objects via RF energy, and/or electromagnetic navigation systems that track objects via electromagnetic signals. Other types of navigation systems are also contemplated. It should also be appreciated that the models described herein may comprise triangulated meshes, volumetric models using voxels, or other types of 3-D and/or 2-D models in some cases.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical robotic system comprising:
a robotic manipulator;
a surgical tool coupled to the robotic manipulator and configured to hold a screw and to rotate the screw about a rotational axis, the screw having a known thread geometry;
a navigation system configured to track a position of a target anatomy; and
one or more controllers coupled to the robotic manipulator and the navigation system and comprising memory for storing the known thread geometry and wherein the one or more controllers are configured to:
control movement of the robotic manipulator to maintain the rotational axis of the surgical tool along a planned trajectory with respect to the target anatomy based on the tracked position of the target anatomy, and
autonomously control a rotational rate of the surgical tool to rotate the screw about the rotational axis and an advancement rate of the surgical tool to linearly advance the screw along the planned trajectory wherein the rotational rate of the surgical tool and the advancement rate of the surgical tool are proportional to the known thread geometry stored in the memory.

2. The surgical robotic system of claim 1, wherein the surgical tool comprises a screw driver.

3. The surgical robotic system of claim 1, wherein the planned trajectory is defined by a haptic object.

4. The surgical robotic system of claim 3, wherein the haptic object comprises a line haptic object, and the one or more controllers are configured to control the robotic manipulator to generate haptic feedback to a user to indicate that the screw has reached a planned insertion depth at the target anatomy.

5. The surgical robotic system of claim 1, wherein the one or more controllers are configured to cause autonomous movement of the surgical tool to place the rotational axis along the planned trajectory.

6. The surgical robotic system of claim 1, comprising a torque sensor to determine a torque being applied to drive the screw, wherein the one or more controllers are configured to stop the surgical tool from driving the screw into the target anatomy once the torque meets or exceeds a torque threshold.

7. The surgical robotic system of claim 6, wherein the torque sensor comprises a current measuring circuit.

8. The surgical robotic system of claim 1, wherein the navigation system comprises a navigation controller, and an imaging device coupled to the navigation controller.

9. The surgical robotic system of claim 8, wherein the navigation system comprises a first tracker to track the surgical tool and a second tracker to track the target anatomy.

10. The surgical robotic system of claim 8, comprising a display coupled to the navigation controller, wherein the navigation controller is configured to output, on the display, information relating to a location of the screw relative to the target anatomy.

11. The surgical robotic system of claim 1, wherein the rotational rate of the surgical tool and the advancement rate of the surgical tool are proportional to the known thread geometry according to a relationship $$\frac{\delta\theta}{\delta t} = \frac{\delta D}{\delta t} * \frac{\text{Pitch}}{2\pi},$$

wherein $$\frac{\delta\theta}{\delta t}$$

is the rotational rate of the surgical tool, $$\frac{\delta D}{\delta t}$$

is the advancement rate of the surgical tool, and Pitch is a number of threads per unit length of the screw.

12. A surgical robotic system comprising:
a robotic manipulator comprising a sensor;
a surgical tool coupled to the robotic manipulator and configured to hold a screw and to rotate the screw about a rotational axis, the screw having a known thread geometry;
a navigation system configured to track a position of a target anatomy; and
one or more controllers coupled to the robotic manipulator and the navigation system and comprising a memory for storing the known thread geometry and wherein the one or more controllers are configured to:
control movement of the robotic manipulator to maintain the rotational axis of the surgical tool on a planned trajectory with respect to the target anatomy based on the tracked position of the target anatomy,
detect, with the sensor, a force applied by a user;
control one of a rotational rate of the surgical tool to insert the screw about the rotational axis or an advancement rate of the surgical tool to insert the screw linearly along the planned trajectory based on the forces applied by the user to implant the screw into the target anatomy; and
autonomously control the other of the advancement rate of the surgical tool or the rotational rate of the surgical tool so that the advancement rate of the surgical tool and the rotational rate of the surgical tool are proportional to the force applied by the user and to the known thread geometry stored in the memory.

13. The surgical robotic system of claim 12, wherein the surgical tool comprises a trigger, the sensor coupled to the trigger and configured to generate a signal indicative of a user's input.

14. The surgical robotic system of claim 13, wherein the one or more controllers control the rotational rate of the surgical tool based on the signal, and autonomously control the advancement rate of the surgical tool to be proportional to the rotational rate of the surgical tool and the known thread geometry.

15. The surgical robotic system of claim 14, wherein the one or more controllers autonomously control the advancement rate of the surgical tool to be proportional to the rotational rate of the surgical tool and the known thread geometry according to a relationship $$\frac{\delta\theta}{\delta t} = \frac{\delta D}{\delta t} * \frac{\text{Pitch}}{2\pi},$$

wherein $$\frac{\delta\theta}{\delta t}$$

is the rotational rate of the surgical tool, $$\frac{\delta D}{\delta t}$$

is the advancement rate of the surgical tool, and Pitch is a number of threads per unit length of the screw.

16. The surgical robotic system of claim 13, wherein the one or more controllers control the advancement rate of the surgical tool based on the signal, and autonomously control the rotational rate of the surgical tool to be proportional to the advancement rate of the surgical tool and the known thread geometry.

17. The surgical robotic system of claim 16, wherein the one or more controllers autonomously control the rotational rate of the surgical tool to be proportional to the advancement rate of the surgical tool and the known thread geometry according to a relationship $$\frac{\delta\theta}{\delta t} = \frac{\delta D}{\delta t} * \frac{\text{Pitch}}{2\pi},$$

wherein $$\frac{\delta\theta}{\delta t}$$

is the rotational rate of the surgical tool, $$\frac{\delta D}{\delta t}$$

is the advancement rate of the surgical tool, and Pitch is a number of threads per unit length of the screw.

* * * * *